United States Patent
Du Bois et al.

(10) Patent No.: US 7,981,914 B2
(45) Date of Patent: *Jul. 19, 2011

(54) TETRAZOLE-SUBSTITUTED ARYL AMIDE DERIVATIVES AND USES THEREOF

(75) Inventors: Daisy Joe Du Bois, Palo Alto, CA (US);
Todd Richard Elworthy, Los Altos, CA (US); Hans Maag, Sausalito, CA (US);
Sunil Sahdeo, San Francisco, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 29 days.

This patent is subject to a terminal disclaimer.

(21) Appl. No.: 12/286,643

(22) Filed: Oct. 1, 2008

(65) Prior Publication Data

US 2009/0093523 A1    Apr. 9, 2009

Related U.S. Application Data

(60) Provisional application No. 60/997,597, filed on Oct. 4, 2007.

(51) Int. Cl.
*A61K 31/44* (2006.01)
*C07D 207/04* (2006.01)
(52) U.S. Cl. .................... 514/381; 548/250
(58) Field of Classification Search .......... 514/381; 548/250
See application file for complete search history.

(56) References Cited

U.S. PATENT DOCUMENTS 7,595,405 B2 *  9/2009  Dillon et al. ............ 548/254
2003/0187076 A1  10/2003  Agoston et al.

FOREIGN PATENT DOCUMENTS

| DE | 100 55 713 A1 | 5/2002 |
| WO | WO 01/02379 A1 | 1/2001 |
| WO | WO 02/00647 A1 | 1/2002 |
| WO | WO 2004/009816 A1 | 1/2004 |
| WO | WO 2004/029050 A1 | 4/2004 |
| WO | WO 2004/094395 A2 | 11/2004 |
| WO | WO 2004/094395 A3 | 11/2004 |
| WO | WO 2008/000645 A1 | 1/2008 |

OTHER PUBLICATIONS

Maelicke et al., Eur. J. Pharm., vol. 393, 2000, pp. 165-170, esp. p. 168.*
Meyer, E. M., et. al. "Neuroprotective effects of 2,4-dimethoxybenzylidene anabaseine (DMXB) and Tetrahydroaminoacridine (THA) in neocortices of nucleus basalis lesioned rats," *Brian Res.* 1998, vol. 786, pp. 252-254.
Rezvani, A. H., et. al. "Effect of R3487/MEM3454, a novel nicotinic α7 receptor partial agonist and 5-HT3 antagonist on sustained attention in rats," *Progress in Neuro-Psychopharmacology and Biological Psychiatry*, 2009, vol. 33 (2), pp. 269-275.
Timmermann, D. B., et. al. "An Allosteric Modulator of the α7 Nicotinic Acetylcholine Receptor Possessing Cognition-Enhancing Properties in Vivo," *J. Pharmacology and Experimental Therap.* 2007, vol. 323 (1), pp. 294-307.

* cited by examiner

*Primary Examiner* — Susannah Chung
(74) *Attorney, Agent, or Firm* — Robert C. Hall

(57) ABSTRACT

Compounds of the formula:

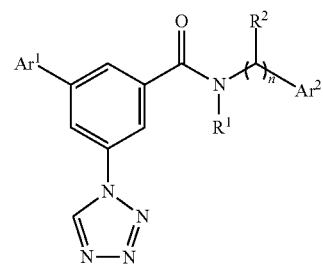

wherein $R^1$, $R^2$, $Ar^1$, $Ar^2$, and n are as defined herein. Also provided are pharmaceutical compositions, methods of using, and methods of preparing the subject compounds.

29 Claims, No Drawings

TETRAZOLE-SUBSTITUTED ARYL AMIDE DERIVATIVES AND USES THEREOF

CROSS REFERENCE TO RELATED APPLICATIONS

This application claims the benefit of priority of U.S. Provisional Patent Application Ser. No. 60/997,597, filed Oct. 4, 2007, the disclosure of which is incorporated herein by reference in its entirety.

FIELD OF THE INVENTION

This invention relates to nicotinic acetylcholine receptors (nAChR), and particularly to positive allosteric modulators for the alpha 7 nAChR subtype, and methods of making and using such compounds.

BACKGROUND OF THE INVENTION

Nicotinic acetylcholine receptors (nAChR) are members of the ligand-gated ion channel family. When activated, the conductance of ions across the nicotinic ion channels increases. Nicotinic alpha 7 receptor (alpha 7 nAChR) forms a homopentameric channel in vitro that is highly permeable to calcium cations. Each alpha 7 nAChR has four transmembrane domains, known as M1, M2, M3, and M4. The M2 domain has been suggested to form the wall lining the channel. Sequence alignment shows that the alpha 7 nAChR is highly conserved during evolution. The M2 domain that lines the channel is identical in protein sequence from chick to human. Alpha 7 nAChR is described by, Revah et al. (1991), *Nature,* 353, 846-849; Galzi et al. (1992), *Nature* 359, 500-505; Fucile et al. (2000), *PNAS* 97(7), 3643-3648; Briggs et al. (1999), *Eur. J. Pharmacol.* 366 (2-3), 301-308; and Gopalakrishnan et al. (1995), *Eur. J. Pharmacol.* 290(3), 237-246.

The alpha 7 nAChR channel is expressed in various brain regions and is believed to be involved in many important biological processes in the central nervous system (CNS), including learning, memory and attention (Levin et al., *Psychopharmacology* (1998), 138, 217-230). Alpha 7 nAChR are localized on both presynaptic and postsynaptic terminals and have been suggested to be involved in modulating synaptic transmission. Agonists of alpha 7 nAChR have been shown to improve attention and cognition in Alzheimer's and attention deficit disorder conditions (Wilens et al., *Am. J Psychiatry* (1999), 156(12), 1931-1937).

The analgesic effects of nicotine have long been known. Agonists of the alpha 7 nAChR receptor have been shown to modulate production of pro-inflammatory cytokines, including interleukins (ILs), tumor necrosis factor (TNF) alpha, and high-mobility group box (HMGB-1), and to inhibit inflammatory signalling in the CNS (de Jonge et al., *Br. J. Pharmacol.* (2007), 1-15). The alpha 7 nAChR receptor has a role in modulating CNS pain transmission, and alpha 7 nAChR agonists have shown an antinociceptive effect in an acute pain model (Damaj et al., *Neuropharmacol.* (2000) 39, 2785-2791.

Since acetylcholine (ACh) is an endogenous agonist of alpha 7 nAChR, agonists that act at the same site as ACh can stimulate and possibly block receptor activity through desensitization and competitive blockade processes (Forman et al., *Biophysical J.* (1988), 54(1), 149-158) and lead to prolonged receptor inactivation (Buisson et al., *J. Neurosci.* (2001), 21(6), 1819-1829). Desensitization limits the duration that the ion channel remains activated during agonist application. Thus the enhancement of Alpha 7 nAChR activity provided by such agonists will also increase competition with ACh, and therefore limit the usefulness of agonists as drugs.

Positive allosteric modulators of the nicotinic alpha 7 receptor channel enhance the activity of ACh and other nicotinic alpha 7 receptor agonists. Positive allosteric modulators activate alpha 7 nAChR when sufficient ACh is present in the central nervous system. Positive allosteric modulators of alpha 7 nAChRs thus are useful for treatment of CNS, pain and inflammatory diseases or conditions, to regulate CNS functions such as cognition, learning, mood, emotion and attention, and control production of pro-inflammatory cytokines associated with pain and inflammatory conditions. There is accordingly a need for new positive allosteric modulators of the the nicotinic alpha 7 receptor channel.

SUMMARY OF THE INVENTION

One aspect of the invention provides compounds of formula I:

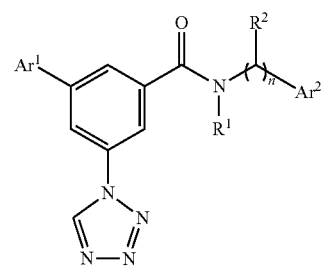

or a pharmaceutically acceptable salt thereof,
wherein:
  n is from 1 to 3;
  $Ar^1$ and $Ar^2$ each independently is optionally substituted aryl or optionally substituted heteroaryl;
  $R^1$ is hydrogen or $C_{1-6}$alkyl;
  $R^2$ is hydrogen, or $R^2$ may form an alkylene bridge with $Ar^2$;
  provided that when $Ar^1$ is 4-methyl-phenyl, 5-methyl-pyridinyl or 5-chloro-pyridinyl, then n is 2 or 3; and
  provided that when n is 2, $R^2$ and $R^3$ are hydrogen and $Ar^1$ is phenyl or 2-methoxy-phenyl, then $Ar^2$ is not 4-methoxy-phenyl or 3,4-dimethoxy-phenyl.

The invention also provides pharmaceutical compositions, methods of using, and methods of preparing the aforementioned compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" means isopropyl, isobutyl, tert-butyl, "Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, tert-butoxy and the like.

"Alkoxyalkyl" means a moiety of the formula —R''—R'', where R' is alkylene and R'' is alkoxy as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —C(O)—R, where R' is alkyl as defined herein.

"Alkylsulfonyl" means a moiety of the formula —$SO_2$—R' where R' is alkyl as defined herein.

"Alkylenedioxy" means a group of the formula

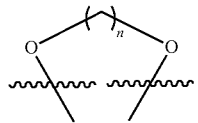

wherein n is 1 (methylenedioxy) or 2 (alkylenedioxy). When an alkylenedioxy is a substituent on an aryl group such as phenyl, the alkylenedioxy occupies two adjacent ring atoms. For example, phenyl substituted with methylenedioxy is benzo[1,3]dioxole, and phenyl substituted with ethylenedioxy is 2,3-dihydro-benzo[1,4]dioxine.

"Amino" means a moiety of the formula —NRR' where R and R' each independently is hydrogen or alkyl as defined herein.

"Aminosulfonyl" means a moiety of the formula —$SO_2$—R' where R' is amino as defined herein.

"Alkylsulfonylalkyl" means a moiety of the formula —$R^b$—$SO_2$—$R^a$, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Alkylsulfonyloxy" means a moiety of the formula $R^a$—$SO_2$—O—, where $R^a$ is alkyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each of which may be optionally substituted. Preferred aryl included optionally substituted phenyl and optionally substituted naphthyl. A preferred aryl is optionally substituted phenyl.

"Aryloxy" means a moiety of the formula —OR, wherein R is an aryl moiety as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Aralkoxy" means a moiety of the formula —OR, wherein R is an aralkyl moiety as defined herein.

"Cyanoalkyl" means a moiety of the formula —R'—R'', where R' is alkylene as defined herein and R'' is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkyloxy" and "cycloalkoxy", which may be used interchangeably, mean a group of the formula —OR wherein R is cycloalkyl as defined herein. Exemplary cycloalkyloxy include cyclopropyloxy, cyclobutyloxy, cyclopentyloxy, cyclohexyloxy and the like.

"Cycloalkylalkyl" means a moiety of the formula —R'—R'', where R' is alkylene and R'' is cycloalkyl as defined herein.

"Cycloalkylalkyloxy" and "cycloalkylalkoxy", which may be used interchangeably, mean a group of the formula —OR wherein R is cycloalkylalkyl as defined herein. Exemplary cycloalkyloxy include cyclopropylmethoxy, cyclobutylmethoxy, cyclopentylmethoxy, cyclohexylmethoxy and the like.

"Heteroalkyl" means an alkyl radical as defined herein, including a branched $C_4$-$C_7$-alkyl, wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic, bicyclic or tricyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof, each of which may be optionally substituted. Preferred heteroaryl include indolyl, pyridinyl, pyrimidinyl, thienyl, furanyl pyrrolyl, imidazolyl and pyrazolyl, each of which may be optionally substituted.

"Heteroarylalkyl" and "heteroaralkyl", which may be used interchangeably, mean a radical-$R^aR^b$ where $R^a$ is an alkylene group and $R^b$ is a heteroaryl group as defined herein The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. Examples of haloalkoxy moieties include, but are not limited to, trifluoromethoxy, difluoromethoxy, 2,2,2-trifluoroethoxy, and the like.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Optionally substituted", when used in association with "aryl", phenyl", "heteroaryl" (including indolyl such as indol-1-yl, indol-2-yl and indol-3-yl, 2,3-dihydroindolyl such as 2,3-dihydroindol-1-yl, 2,3-dihydroindol-2-yl and 2,3-dihydroindol-3-yl, indazolyl such as indazol-1-yl, indazol-2-yl and indazol-3-yl, benzimidazolyl such as benzimidazol-1-yl and benzimidazol-2-yl, benzofuranyl such as benzofuran-2-yl and benzofuran-3-yl, benzothiophenyl such as benzothiophen-2-yl and benzothiophen-3-yl, benzoxazol-2-yl, benzothiazol-2-yl, thienyl, furanyl, pyridinyl, pyrimidinyl, pyridazinyl, pyrazinyl, oxazolyl, thiazolyl, isoxazolyl, isothiazolyl, imidazolyl, pyrazolyl and quinolinyl)" or "heterocyclyl", means an aryl, phenyl, heteroaryl or heterocyclyl which is optionally substituted independently with one to four substituents, preferably one or two substituents selected from alkyl, cycloalkyl, alkoxy, halo, haloalkyl, haloalkoxy, cyano, nitro, heteroalkyl, amino, mono-alkylamino, di-alkylamino, hydroxyalkyl, alkoxyalkyl, alkylsulfonyl, alkylsulfonamido, benzyloxy, cycloalkylalkyl, cycloalkoxy, cycloalkylalkoxy, alkylsulfonyloxy, optionally substituted thienyl, optionally substituted pyrazolyl, optionally substituted pyridinyl, morpholinocarbonyl, —$(CH_2)_q$—$S(O)_rR^f$; —$(CH_2)_q$—$NR^gR^h$; —$(CH_2)_q$—$C(=O)$—$NR^gR^h$; —$(CH_2)_q$—$C(=O)$—$NR^gR^h$; —$(CH_2)_q$—$C(=O)$—$C(=O)$—$NR^gR^h$; —$(CH_2)_q$—$SO_2$—$NR^gR^h$; —$(CH_2)_q$—$N(R^f)$—$C(=O)$—$R^i$; —$(CH_2)_q$—$C(=O)$—$R^i$; or —$(CH_2)_q$—$N(R^f)$—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy. Certain preferred optional substituents for "aryl", phenyl", "heteroaryl" "cycloalkyl" or "heterocyclyl" include alkyl, halo, haloalkyl, alkoxy, cyano, amino, aminosulfonyl, and alkylsulfonyl. More preferred substituents are methyl, fluoro, chloro, trifluoromethyl, methoxy, amino, aminosulfonyl and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Pain" and pain conditions (states) as used herein means pain associated with any of a wide variety of causes, including but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

"Inflammation" means any pathological process characterized by injury or destruction of tissues resulting from cytologic reactions, chemical reactions or other causes. Inflammation may be manifested by signs of pain, heat, redness, swelling, and loss of function. Inflammation indications include, but are not limited to, bacterial, fungal or viral infections, rheumatoid arthritis, osteoarthritis, surgery, bladder infection or idiopathic bladder inflammation, over-use, old age, or nutritional deficiencies, prostatis and conjunctivitis.

"Cognition" means any mental process associated with acquiring and retaining knowledge. A "cognition disorder" means any disturbance to the mental process or processes related to thinking, reasoning, judgment ad memory. Cognition disorders may result from or other wise be associated with Parkinson's disease, Huntington's disease, anxiety, depression, manic depression, psychosis, epilepsy, obsessive compulsive disorders, mood disorders, migraine, Alzheimer's disease, sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen, sulfur or nitrogen atom in the structures herein indicates the presence of a hydrogen atom.

Whenever a chiral carbon is present in a chemical structure, it is intended that all stereoisomers associated with that chiral carbon are encompassed by the structure.

All patents and publications identified herein are incorporated herein by reference in their entirety.

Compounds of the Invention

The invention provides compounds of formula I:

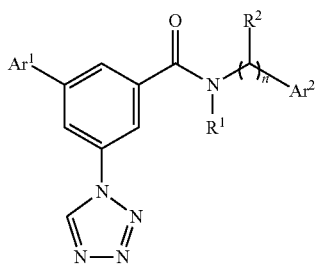

I or a pharmaceutically acceptable salt thereof,
wherein:
  n is from 1 to 3;
  $Ar^1$ and $Ar^2$ each independently is optionally substituted aryl or optionally substituted heteroaryl;
  $R^1$ is hydrogen or $C_{1-6}$alkyl;
  $R^2$ is hydrogen, or $R^2$ may form an alkylene bridge with $Ar^2$;
  provided that when $Ar^1$ is 4-methyl-phenyl, 5-methyl-pyridinyl or 5-chloro-pyridinyl, then n is 2 or 3; and
  provided that when n is 2, $R^2$ and $R^3$ are hydrogen and $Ar^1$ is phenyl or 2-methoxy-phenyl, then $Ar^2$ is not 4-methoxy-phenyl or 3,4-dimethoxy-phenyl.

In certain embodiments of formula I, n is 1.
In certain embodiments of formula I, n is 2.
In certain embodiments of formula I, n is 3.
In certain embodiments of formula I, $R^1$ is hydrogen.
In certain embodiments of formula I, $R^2$ is hydrogen.
In certain embodiments of formula I, $Ar^1$ is optionally substituted aryl.
In certain embodiments of formula I, $Ar^1$ is optionally substituted phenyl.
In certain embodiments of formula I, $Ar^1$ is phenyl optionally substituted one, two or three times, preferably once or twice, with a group or groups independently selected from halo, $C_{1-6}$alkyl, $C_{1-6}$alkoxy, halo-$C_{1-6}$alkyl, $C_{1-6}$alkyl-carbonyl, $C_{1-6}$alkoxy-carbonyl, $C_{1-6}$alkyl-sulfonyl $C_{1-6}$alkyl-sulfanyl, amino, hydroxy-$C_{1-6}$alkyl, hydroxy, alkylenedioxy and cyano.

In certain embodiments of formula I, $Ar^1$ is phenyl optionally substituted once or twice with a group or groups independently selected from fluoro, chloro, methyl, ethyl, methoxy, ethoxy, acetyl, methanesulfonyl, methanesulfanyl, hydroxymethyl, hydroxy, ethoxycarbonyl and cyano.

In certain embodiments of formula I, $Ar^1$ is phenyl, 2-methoxy-phenyl, 3-methoxy-phenyl, 4-methoxy-phenyl, 2-chloro-phenyl, 3-chloro-phenyl, 4-chloro-phenyl, 2-methyl-phenyl, 3-methyl-phenyl, 4-methyl-phenyl, 2-fluoro-phenyl, 3-fluoro-phenyl, 4-fluoro-phenyl, 2-ethoxy-phenyl, 2-acetyl-phenyl, 2,3-dimethoxy-phenyl, 2,4-dimethoxy-phenyl, 2,5-dimethoxy-phenyl, 3,4-dimethoxy-phenyl, 3,5-dimethoxy-phenyl, 3,6-dimethoxy-phenyl, 2,3-dichloro-phenyl, 2,4-dichloro-phenyl, 2,5-dichloro-phenyl, 3,4-dichloro-phenyl, 3,5-dichloro-phenyl, 3,6-dichloro-phenyl, 2,3-difluoro-phenyl, 2,4-difluoro-phenyl, 2,5-difluoro-phenyl, 3,4-difluoro-phenyl, 3,5-difluoro-phenyl, 3,6-difluoro-phenyl, 2,3-dimethyl-phenyl, 2,4-dimethyl-phenyl, 2,5-dimethyl-phenyl, 3,4-dimethyl-phenyl, 3,5-dimethyl-phenyl, 3,6-dimethyl-phenyl, 3-chloro-2-methoxy-phenyl, 4-chloro-2-methoxy-phenyl, 5-chloro-2-methoxy-phenyl, 6-chloro-2-methoxy-phenyl, 2-chloro-3-methoxy-phenyl, 4-chloro-3-methoxy-phenyl, 5-chloro-3-methoxy-phenyl, 6-chloro-3-methoxy-phenyl, 2-chloro-4-methoxy-phenyl, 2-chloro-5-methoxy-phenyl, 3-fluoro-2-methoxy-phenyl, 4-fluoro-2-methoxy-phenyl, 5-fluoro-2-methoxy-phenyl, 6-fluoro-2-methoxy-phenyl, 2-fluoro-3-methoxy-phenyl, 4-fluoro-3-methoxy-phenyl, 5-fluoro-3-methoxy-phenyl, 6-fluoro-3-methoxy-phenyl, 2-fluoro-4-methoxy-phenyl, 2-fluoro-5-methoxy-phenyl, 3-methyl-2-methoxy-phenyl, 4-methyl-2-methoxy-phenyl, 5-methyl-2-methoxy-phenyl, 6-methyl-2-methoxy-phenyl, 2-methyl-3-methoxy-phenyl, 4-methyl-3-methoxy-phenyl, 5-methyl-3-methoxy-phenyl, 6-methyl-3-methoxy-phenyl, 2-methyl-4-methoxy-phenyl, 2-methyl-5-methoxy-phenyl, 2-methanesulfanyl-phenyl, 2-methanesulfonyl-phenyl, 2-hydroxy-phenyl, 4-ethoxycarbonyl-phenyl, 2-ethyl-phenyl, 2-cyano-phenyl, or 4-methanesulfonyl-phenyl.

In certain embodiments of formula I, $Ar^1$ is 3-methoxy-phenyl, 4-methoxy-phenyl, 2-chloro-phenyl, 3-chloro-phenyl, 4-chloro-phenyl, 2-methyl-phenyl, 3-methyl-phenyl, 4-methyl-phenyl, 2-fluoro-phenyl, 3-fluoro-phenyl, 4-fluoro-phenyl, 2-ethoxy-phenyl, 2-acetyl-phenyl, 2,3-dimethoxy-phenyl, 2,4-dimethoxy-phenyl, 2,5-dimethoxy-phenyl, 3,4-dimethoxy-phenyl, 3,5-dimethoxy-phenyl, 3,6-dimethoxy-phenyl, 2,3-dichloro-phenyl, 2,4-dichloro-phenyl, 2,5-dichloro-phenyl, 3,4-dichloro-phenyl, 3,5-dichloro-phenyl, 3,6-dichloro-phenyl, 2,3-difluoro-phenyl, 2,4-difluoro-phenyl, 2,5-difluoro-phenyl, 3,4-difluoro-phenyl, 3,5-difluoro-phenyl, 3,6-difluoro-phenyl, 2,3-dimethyl-phenyl, 2,4-dimethyl-phenyl, 2,5-dimethyl-phenyl, 3,4-dimethyl-phenyl, 3,5-dimethyl-phenyl, 3,6-dimethyl-phenyl, 3-chloro-2-methoxy-phenyl, 4-chloro-2-methoxy-phenyl, 5-chloro-2-methoxy-phenyl, 6-chloro-2-methoxy-phenyl, 2-chloro-3-methoxy-phenyl, 4-chloro-3-methoxy-phenyl, 5-chloro-3-methoxy-phenyl, 6-chloro-3-methoxy-phenyl, 2-chloro-4-methoxy-phenyl, 2-chloro-5-methoxy-phenyl, 3-fluoro-2-methoxy-phenyl, 4-fluoro-2-methoxy-phenyl, 5-fluoro-2-methoxy-phenyl, 6-fluoro-2-methoxy-phenyl, 2-fluoro-3-methoxy-phenyl, 4-fluoro-3-methoxy-phenyl, 5-fluoro-3-methoxy-phenyl, 6-fluoro-3-methoxy-phenyl, 2-fluoro-4-methoxy-phenyl, 2-fluoro-5-methoxy-phenyl, 3-methyl-2-methoxy-phenyl, 4-methyl-2-methoxy-phenyl, 5-methyl-2-methoxy-phenyl, 6-methyl-2-methoxy-phenyl, 2-methyl-3-methoxy-phenyl, 4-methyl-3-methoxy-phenyl, 5-methyl-3-methoxy-phenyl, 6-methyl-3-methoxy-phenyl, 2-methyl-4-methoxy-phenyl, 2-methyl-5-methoxy-phenyl, 2-methanesulfanyl-phenyl, 2-methanesulfonyl-phenyl, 2-hydroxy-phenyl, 4-ethoxycarbonyl-phenyl, 2-ethyl-phenyl, 2-cyano-phenyl, or 4-methanesulfonyl-phenyl.

In certain embodiments of formula I, $Ar^1$ is phenyl, 2-methoxy-phenyl, 4-methoxy-phenyl, 4-chloro-phenyl, 4-methyl-phenyl, 2-methyl-phenyl, 2-chloro-phenyl, 2-fluoro-phenyl, 2-ethoxy-phenyl, 2-acetyl-phenyl, 2,4-dimethoxy-phenyl, 3,6-dimethoxy-phenyl, 5-fluoro-2-methoxy-phenyl, 5-chloro-2-methoxy-phenyl, 2,5-dichloro-phenyl, 2-hydroxymethyl-phenyl, 2,3-dichloro-phenyl, 2-methanesulfanyl-phenyl, 2,3-difluoro-phenyl, 2,4-dichloro-phenyl, 2-hydroxy-phenyl, 4-ethoxycarbonyl-phenyl, 2-ethyl-phenyl, 2-cyano-phenyl, 2,3-dimethoxy-phenyl, 4-methoxy-2-methyl-phenyl or 4-methanesulfonyl-phenyl.

In certain embodiments of formula I, $Ar^1$ is 4-methoxy-phenyl, 4-chloro-phenyl, 4-methyl-phenyl, 2-methyl-phenyl, 2-chloro-phenyl, 2-fluoro-phenyl, 2-ethoxy-phenyl, 2-acetyl-phenyl, 2,4-dimethoxy-phenyl, 3,6-dimethoxy-phenyl, 5-fluoro-2-methoxy-phenyl, 5-chloro-2-methoxy-phenyl, 2,5-dichloro-phenyl, 2-hydroxymethyl-phenyl, 2,3-dichloro-phenyl, 2-methanesulfanyl-phenyl, 2,3-difluoro-phenyl, 2,4-dichloro-phenyl, 2-hydroxy-phenyl, 4-ethoxycarbonyl-phenyl, 2-ethyl-phenyl, 2-cyano-phenyl, 2,3-dimethoxy-phenyl, 4-methoxy-2-methyl-phenyl or 4-methanesulfonyl-phenyl.

In certain embodiments of formula I, $Ar^1$ is 2-methoxy-phenyl that is optionally substituted once at the 3-, 4-, 5- or 6-position with fluoro, chloro, methyl or methoxy.

In certain embodiments of formula I, $Ar^1$ is 2-methoxy-phenyl that is substituted once at the 3-, 4-, 5- or 6-position with fluoro, chloro, methyl or methoxy.

In certain embodiments of formula I, $Ar^1$ is 2-methoxy-phenyl.

In certain embodiments of formula I, $Ar^1$ is optionally substituted heteroaryl.

In certain embodiments of formula I, $Ar^1$ is pyridinyl, pyrimidinyl, thiophenyl or pyrrolyl, each optionally substituted once or twice with a group or groups independently selected from halo, $C_{1-6}$alkyl, $C_{1-6}$alkoxy, halo-$C_{1-6}$alkyl, $C_{1-6}$alkyl-carbonyl, $C_{1-6}$alkoxy-carbonyl, $C_{1-6}$alkyl-sulfonyl, aminosulfonyl, $C_{1-6}$alkyl-sulfanyl, hydroxy-$C_{1-6}$alkyl, amino, hydroxy, alkylenedioxy and cyano.

In certain embodiments of formula I, $Ar^1$ is pyridinyl, pyrimidinyl, thiophenyl or pyrrolyl, each optionally substituted once or twice with a group or groups independently selected from fluoro, chloro, methyl, ethyl, methoxy, ethoxy, acetyl, methanesulfonyl, methanesulfanyl, hydroxymethyl, ethoxycarbonyl and cyano.

In certain embodiments of formula I, $Ar^1$ is optionally substituted pyridinyl.

In certain embodiments of formula I, $Ar^1$ is pyridinyl optionally substituted once or twice with a group or groups independently selected from halo, $C_{1-6}$alkyl, $C_{1-6}$alkoxy, halo-$C_{1-6}$alkyl, $C_{1-6}$alkyl-carbonyl, $C_{1-6}$alkoxy-carbonyl, $C_{1-6}$alkyl-sulfonyl, aminosulfonyl, $C_{1-6}$alkyl-sulfanyl, hydroxy-$C_{1-6}$alkyl, amino, hydroxy, alkylenedioxy and cyano.

In certain embodiments of formula I, $Ar^1$ is pyridinyl optionally substituted once or twice with a group or groups independently selected from fluoro, chloro, methyl, ethyl, methoxy, ethoxy, acetyl, methanesulfonyl, methanesulfanyl, hydroxymethyl, ethoxycarbonyl and cyano.

In certain embodiments of formula I, $Ar^1$ is pyridin-2-yl or pyridin-3-yl optionally substituted with methoxy or trifluoromethyl.

In certain embodiments of formula I, $Ar^1$ is 3-methoxy-pyridin-2-yl, 5-trifluoromethyl-pyridin-2-yl or 2-methoxy-pyridin-3-yl.

In certain embodiments of formula I, $Ar^2$ is optionally substituted phenyl.

In certain embodiments of formula I, $Ar^2$ is phenyl optionally substituted once or twice with a group or groups independently selected from halo, $C_{1-6}$alkyl, $C_{1-6}$alkoxy, halo-$C_{1-6}$ alkyl, $C_{1-6}$alkyl-carbonyl, $C_{1-6}$alkoxy-carbonyl, $C_{1-6}$alkyl-sulfonyl, $C_{1-6}$alkyl-sulfanyl, hydroxy-$C_{1-6}$alkyl, amino, hydroxy, alkylenedioxy and cyano.

In certain embodiments of formula I, $Ar^2$ is phenyl optionally substituted once or twice with a group or groups independently selected from fluoro, chloro, bromo, methyl, methoxy, aminosulfonyl, dimethylamino, methanesulfonyl or methylenedioxy.

In certain embodiments of formula I, $Ar^2$ is phenyl, 2-methoxy-phenyl, 3-methoxy-phenyl, 4-methoxy-phenyl, 2-chloro-phenyl, 3-chloro-phenyl, 4-chloro-phenyl, 2-methyl-phenyl, 3-methyl-phenyl, 4-methyl-phenyl, 2-fluoro-phenyl, 3-fluoro-phenyl, 4-fluoro-phenyl, 2-ethoxy-phenyl, 2-acetyl-phenyl, 2,3-dimethoxy-phenyl, 2,4-dimethoxy-phenyl, 2,5-dimethoxy-phenyl, 3,4-dimethoxy-phenyl, 3,5-dimethoxy-phenyl, 3,6-dimethoxy-phenyl, 2,3-dichloro-phenyl, 2,4-dichloro-phenyl, 2,5-dichloro-phenyl, 3,4-dichloro-phenyl, 3,5-dichloro-phenyl, 3,6-dichloro-phenyl, 2,3-difluoro-phenyl, 2,4-difluoro-phenyl, 2,5-difluoro-phenyl, 3,4-difluoro-phenyl, 3,5-difluoro-phenyl, 3,6-difluoro-phenyl, 2,3-dimethyl-phenyl, 2,4-dimethyl-phenyl, 2,5-dimethyl-phenyl, 3,4-dimethyl-phenyl, 3,5-dimethyl-phenyl, 3,6-dimethyl-phenyl, 3-chloro-2-methoxy-phenyl, 4-chloro-2-methoxy-phenyl, 5-chloro-2-methoxy-phenyl, 6-chloro-2-methoxy-phenyl, 2-chloro-3-methoxy-phenyl, 4-chloro-3-methoxy-phenyl, 5-chloro-3-methoxy-phenyl, 6-chloro-3-methoxy-phenyl, 2-chloro-4-methoxy-phenyl, 2-chloro-5-methoxy-phenyl, 3-fluoro-2-methoxy-phenyl, 4-fluoro-2-methoxy-phenyl, 5-fluoro-2-methoxy-phenyl, 6-fluoro-2-methoxy-phenyl, 2-fluoro-3-methoxy-phenyl, 4-fluoro-3-methoxy-phenyl, 5-fluoro-3-methoxy-phenyl, 6-fluoro-3-methoxy-phenyl, 2-fluoro-4-methoxy-phenyl, 2-fluoro-5-methoxy-phenyl, 3-methyl-2-methoxy-phenyl, 4-methyl-2-methoxy-phenyl, 5-methyl-2-methoxy-phenyl, 6-methyl-2-methoxy-phenyl, 2-methyl-3-methoxy-phenyl, 4-methyl-3-methoxy-phenyl, 5-methyl-3-methoxy-phenyl, 6-methyl-3-methoxy-phenyl, 2-methyl-4-methoxy-phenyl, 2-methyl-5-methoxy-phenyl, 2-methanesulfanyl-phenyl, 2-hydroxy-phenyl, 4-ethoxycarbonyl-phenyl, 2-ethyl-phenyl, 2-cyano-phenyl, 4-methanesulfonyl-phenyl, 4-aminosulfonyl-phenyl, 4-dimethylamino-phenyl or 3-bromo-4-methoxy-phenyl.

In certain embodiments of formula I, $Ar^2$ is phenyl, 2-methoxy-phenyl, 3-methoxy-phenyl, 4-methoxy-phenyl, 2-chloro-phenyl, 3-chloro-phenyl, 4-chloro-phenyl, 2-methyl-phenyl, 3-methyl-phenyl, 4-methyl-phenyl, 2-fluoro-phenyl, 3-fluoro-phenyl, 4-fluoro-phenyl, 2-ethoxy-phenyl, 2-acetyl-phenyl, 2,3-dimethoxy-phenyl, 2,4-dimethoxy-phenyl, 2,5-dimethoxy-phenyl, 3,5-dimethoxy-phenyl, 3,6-dimethoxy-phenyl, 2,3-dichloro-phenyl, 2,4-dichloro-phenyl, 2,5-dichloro-phenyl, 3,4-dichloro-phenyl, 3,5-dichloro-phenyl, 3,6-dichloro-phenyl, 2,3-difluoro-phenyl, 2,4-difluoro-phenyl, 2,5-difluoro-phenyl, 3,4-difluoro-phenyl, 3,5-difluoro-phenyl, 3,6-difluoro-phenyl, 2,3-dimethyl-phenyl, 2,4-dimethyl-phenyl, 2,5-dimethyl-phenyl, 3,4-dimethyl-phenyl, 3,5-dimethyl-phenyl, 3,6-dimethyl-phenyl, 3-chloro-2-methoxy-phenyl, 4-chloro-2-methoxy-phenyl, 5-chloro-2-methoxy-phenyl, 6-chloro-2-methoxy-phenyl, 2-chloro-3-methoxy-phenyl, 4-chloro-3-methoxy-phenyl, 5-chloro-3-methoxy-phenyl, 6-chloro-3-methoxy-phenyl, 2-chloro-4-methoxy-phenyl, 2-chloro-5-methoxy-phenyl, 3-fluoro-2-methoxy-phenyl, 4-fluoro-2-methoxy-phenyl, 5-fluoro-2-methoxy-phenyl, 6-fluoro-2-methoxy-phenyl, 2-fluoro-3-methoxy-phenyl, 4-fluoro-3-methoxy-phenyl, 5-fluoro-3-methoxy-phenyl, 6-fluoro-3-methoxy-phenyl, 2-fluoro-4-methoxy-phenyl, 2-fluoro-5-methoxy-phenyl, 3-methyl-2-methoxy-phenyl, 4-methyl-2-methoxy-phenyl, 5-methyl-2-methoxy-phenyl, 6-methyl-2-methoxy-phenyl, 2-methyl-3-methoxy-phenyl, 4-methyl-3-methoxy-phenyl, 5-methyl-3-methoxy-phenyl, 6-methyl-3-methoxy-phenyl, 2-methyl-4-methoxy-phenyl, 2-methyl-5-methoxy-phenyl, 2-methanesulfanyl-phenyl, 2-hydroxy-phenyl, 4-ethoxycarbonyl-phenyl, 2-ethyl-phenyl, 2-cyano-phenyl, 4-methanesulfonyl-phenyl, 4-aminosulfonyl-phenyl, 4-dimethylamino-phenyl or 3-bromo-4-methoxy-phenyl.

In certain embodiments of formula I, $Ar^2$ is phenyl, 3-methoxy-phenyl, 4-methoxy-phenyl, 3,4-dimethoxy-phenyl, 4-aminosulfonyl-phenyl, 4-chloro-phenyl, 3,4-dichloro-phenyl, 3-bromo-4-methoxy-phenyl, 2-fluoro-phenyl, 3,4-difluoro-phenyl, 4-methyl-phenyl, 3-methyl-phenyl, 4-fluoro-phenyl, 4-dimethylamino-phenyl, 2-methyl-phenyl, 3,4-ethylenedioxy-phenyl or 4-methanesulfonylphenyl.

In certain embodiments of formula I, $Ar^2$ is phenyl, 3-methoxy-phenyl, 4-methoxy-phenyl, 4-aminosulfonyl-phenyl, 4-chloro-phenyl, 3,4-dichloro-phenyl, 3-bromo-4-methoxy-phenyl, 2-fluoro-phenyl, 3,4-difluoro-phenyl, 4-methyl-phenyl, 3-methyl-phenyl, 4-fluoro-phenyl, 4-dimethylamino-phenyl, 2-methyl-phenyl, 3,4-ethylenedioxy-phenyl or 4-methanesulfonylphenyl.

In certain embodiments of formula I, $Ar^2$ is optionally substituted heteroaryl.

In certain embodiments of formula I, $Ar^2$ is pyridinyl, pyrimidinyl, thiophenyl or pyrrolyl, each optionally substituted once or twice with a group or groups independently selected from halo, $C_{1-6}$alkyl, $C_{1-6}$alkoxy, halo-$C_{1-6}$alkyl, $C_{1-6}$alkyl-carbonyl, $C_{1-6}$alkoxy-carbonyl, $C_{1-6}$alkyl-sulfonyl, aminosulfonyl, $C_{1-6}$alkyl-sulfanyl, hydroxy-$C_{1-6}$alkyl, amino, hydroxy, alkylenedioxy and cyano.

In certain embodiments of formula I, $Ar^2$ is pyridinyl, pyrimidinyl, thiophenyl or pyrrolyl, each optionally substituted once or twice with a group or groups independently selected from fluoro, chloro, methyl, ethyl, methoxy, ethoxy, acetyl, methanesulfonyl, methanesulfanyl, hydroxymethyl, ethoxycarbonyl and cyano.

In certain embodiments of formula I, $Ar^2$ is optionally substituted pyridinyl.

In certain embodiments of formula I, $Ar^2$ is pyridinyl optionally substituted once or twice with a group or groups independently selected from halo, $C_{1-6}$alkyl, $C_{1-6}$alkoxy, halo-$C_{1-6}$alkyl, $C_{1-6}$alkyl-carbonyl, $C_{1-6}$alkoxy-carbonyl, $C_{1-6}$alkyl-sulfonyl, $C_{1-6}$alkyl-sulfanyl, hydroxy-$C_{1-6}$alkyl, amino, hydroxy, alkylenedioxy and cyano.

In certain embodiments of formula I, $Ar^2$ is pyridinyl optionally substituted once or twice with a group or groups independently selected from fluoro, chloro, bromo, methyl, methoxy, aminosulfonyl, methanesulfonyl or methylenedioxy.

In certain embodiments of formula I, $Ar^2$ is pyridin-2-yl, pyridin-3-yl or pyridin-4-yl.

In certain embodiments the invention provides compounds of formula I wherein:
n is 2 or 3;
$R^1$ is hydrogen;
$R^2$ is hydrogen;
$Ar^1$ is 2-methoxy-phenyl, 3-methoxy-phenyl, 4-methoxy-phenyl, 2-chloro-phenyl, 3-chloro-phenyl, 4-chloro-phenyl, 2-methyl-phenyl, 3-methyl-phenyl, 4-methyl-phenyl, 2-fluoro-phenyl, 3-fluoro-phenyl, 4-fluoro-phenyl, 2-ethoxy-phenyl, 2-acetyl-phenyl, 2,3-dimethoxy-phenyl, 2,4-dimethoxy-phenyl, 2,5-dimethoxy-phenyl, 3,4-dimethoxy-phenyl, 3,5-dimethoxy-phenyl, 3,6-dimethoxy-phenyl, 2,3-dichloro-phenyl, 2,4-dichloro-phenyl, 2,5-dichloro-phenyl, 3,4-dichloro-phenyl, 3,5-dichloro-phenyl, 3,6-dichloro-phenyl, 2,3-difluoro-phenyl, 2,4-difluoro-phenyl, 2,5-difluoro-phenyl, 3,4-difluoro-phenyl, 3,5-difluoro-phenyl, 3,6-difluoro-phenyl, 2,3-dimethyl-phenyl, 2,4-dimethyl-phenyl, 2,5-dimethyl-phenyl, 3,4-dimethyl-phenyl, 3,5-dimethyl-phenyl, 3,6-dimethyl-phenyl, 3-chloro-2-methoxy-phenyl, 4-chloro-2-methoxy-phenyl, 5-chloro-2-methoxy-phenyl, 6-chloro-2-methoxy-phenyl, 2-chloro-3-methoxy-phenyl, 4-chloro-3-methoxy-phenyl, 5-chloro-3-methoxy-phenyl, 6-chloro-3-methoxy-phenyl, 2-chloro-4-methoxy-phenyl, 2-chloro-5-methoxy-phenyl, 3-fluoro-2-methoxy-phenyl, 4-fluoro-2-methoxy-phenyl, 5-fluoro-2-methoxy-phenyl, 6-fluoro-2-methoxy-phenyl, 2-fluoro-3-methoxy-phenyl, 4-fluoro-3-methoxy-phenyl, 5-fluoro-3-methoxy-phenyl, 6-fluoro-3-methoxy-phenyl, 2-fluoro-4-methoxy-phenyl, 2-fluoro-5-methoxy-phenyl, 3-methyl-2-methoxy-phenyl, 4-methyl-2-methoxy-phenyl, 5-methyl-2-methoxy-phenyl, 6-methyl-2-methoxy-phenyl, 2-methyl-3-methoxy-phenyl, 4-methyl-3-methoxy-phenyl, 5-methyl-3-methoxy-phenyl, 6-methyl-3-methoxy-phenyl, 2-methyl-4-methoxy-phenyl, 2-methyl-5-methoxy-phenyl, 2-methanesulfanyl-phenyl, 2-methanesulfonyl-phenyl, 2-hydroxy-phenyl, 4-ethoxycarbonyl-phenyl, 2-ethyl-phenyl, 2-cyano-phenyl, or 4-methanesulfonyl-phenyl; and $Ar^2$ is phenyl, 2-methoxy-phenyl, 3-methoxy-phenyl, 4-methoxy-phenyl, 2-chloro-phenyl, 3-chloro-phenyl, 4-chloro-phenyl, 2-methyl-phenyl, 3-methyl-phenyl, 4-methyl-phenyl, 2-fluoro-phenyl, 3-fluoro-phenyl, 4-fluoro-phenyl, 2-ethoxy-phenyl, 2-acetyl-phenyl, 2,3-dimethoxy-phenyl, 2,4-dimethoxy-phenyl, 2,5-dimethoxy-phenyl, 3,5-dimethoxy-phenyl, 3,6-dimethoxy-phenyl, 2,3-dichloro-phenyl, 2,4-dichloro-phenyl, 2,5-dichloro-phenyl, 3,4-dichloro-phenyl, 3,5-dichloro-phenyl, 3,6-dichloro-phenyl, 2,3-difluoro-phenyl, 2,4-difluoro-phenyl, 2,5-difluoro-phenyl, 3,4-difluoro-phenyl, 3,5-difluoro-phenyl, 3,6-difluoro-phenyl, 2,3-dimethyl-phenyl, 2,4-dimethyl-phenyl, 2,5-dimethyl-phenyl, 3,4-dimethyl-phenyl, 3,5-dimethyl-phenyl, 3,6-dimethyl-phenyl, 3-chloro-2-methoxy-phenyl, 4-chloro-2-methoxy-phenyl, 5-chloro-2-methoxy-phenyl, 6-chloro-2-methoxy-phenyl, 2-chloro-3-methoxy-phenyl, 4-chloro-3-methoxy-phenyl, 5-chloro-3-methoxy-phenyl, 6-chloro-3-methoxy-phenyl, 2-chloro-4-methoxy-phenyl, 2-chloro-5-methoxy-phenyl, 3-fluoro-2-methoxy-phenyl, 4-fluoro-2-methoxy-phenyl, 5-fluoro-2-methoxy-phenyl, 6-fluoro-2-methoxy-phenyl, 2-fluoro-3-methoxy-phenyl, 4-fluoro-3-methoxy-phenyl, 5-fluoro-3-methoxy-phenyl, 6-fluoro-3-methoxy-phenyl, 2-fluoro-4-methoxy-phenyl, 2-fluoro-5-methoxy-phenyl, 3-methyl-2-methoxy-phenyl, 4-methyl-2-methoxy-phenyl, 5-methyl-2-methoxy-phenyl, 6-methyl-2-methoxy-phenyl, 2-methyl-3-methoxy-phenyl, 4-methyl-3-methoxy-phenyl, 5-methyl-3-methoxy-phenyl, 6-methyl-3-methoxy-phenyl, 2-methyl-4-methoxy-phenyl, 2-methyl-5-methoxy-phenyl, 2-methanesulfanyl-phenyl, 2-hydroxy-phenyl, 4-ethoxycarbonyl-phenyl, 2-ethyl-phenyl, 2-cyano-phenyl, 4-methanesulfonyl-phenyl, 4-aminosulfonyl-phenyl, 4-dimethylamino-phenyl or 3-bromo-4-methoxy-phenyl.

In certain embodiments the invention provides compounds of formula I wherein:
n is 2 or 3;
$R^1$ is hydrogen;
$R^2$ is hydrogen;
$Ar^1$ is 3-methoxy-phenyl, 4-methoxy-phenyl, 2-chloro-phenyl, 3-chloro-phenyl, 4-chloro-phenyl, 2-methyl-phenyl, 3-methyl-phenyl, 4-methyl-phenyl, 2-fluoro-phenyl, 3-fluoro-phenyl, 4-fluoro-phenyl, 2-ethoxy-phenyl, 2-acetyl-phenyl, 2,3-dimethoxy-phenyl, 2,4-dimethoxy-phenyl, 2,5-dimethoxy-phenyl, 3,4- dimethoxy-phenyl, 3,5-dimethoxy-phenyl, 3,6-dimethoxy-phenyl, 2,3-dichloro-phenyl, 2,4-dichloro-phenyl, 2,5-dichloro-phenyl, 3,4-dichloro-phenyl, 3,5-dichloro-phenyl, 3,6-dichloro-phenyl, 2,3-difluoro-phenyl, 2,4-difluoro-phenyl, 2,5-difluoro-phenyl, 3,4-difluoro-phenyl, 3,5-difluoro-phenyl, 3,6-difluoro-phenyl, 2,3-dimethyl-phenyl, 2,4-dimethyl-phenyl, 2,5-dimethyl-phenyl, 3,4-dimethyl-phenyl, 3,5-dimethyl-phenyl, 3,6-dimethyl-phenyl, 3-chloro-2-methoxy-phenyl, 4-chloro-2-methoxy-phenyl, 5-chloro-2-methoxy-phenyl, 6-chloro-2-methoxy-phenyl, 2-chloro-3-methoxy-phenyl, 4-chloro-3-methoxy-phenyl, 5-chloro-3-methoxy-phenyl, 6-chloro-3-methoxy-phenyl, 2-chloro-4-methoxy-phenyl, 2-chloro-5-methoxy-phenyl, 3-fluoro-2-methoxy-phenyl, 4-fluoro-2-methoxy-phenyl, 5-fluoro-2-methoxy-phenyl, 6-fluoro-2-methoxy-phenyl, 2-fluoro-3-methoxy-phenyl, 4-fluoro-3-methoxy-phenyl, 5-fluoro-3-methoxy-phenyl, 6-fluoro-3-methoxy-phenyl, 2-fluoro-4-methoxy-phenyl, 2-fluoro-5-methoxy-phenyl, 3-methyl-2-methoxy-phenyl, 4-methyl-2-methoxy-phenyl, 5-methyl-2-methoxy-phenyl, 6-methyl-2-methoxy-phenyl, 2-methyl-3-methoxy-phenyl, 4-methyl-3-methoxy-phenyl, 5-methyl-3-methoxy-phenyl, 6-methyl-3-methoxy-phenyl, 2-methyl-4-methoxy-phenyl, 2-methyl-5-methoxy-phenyl, 2-methanesulfanyl-phenyl, 2-methanesulfonyl-phenyl, 2-hydroxy-phenyl, 4-ethoxycarbonyl-phenyl, 2-ethyl-phenyl, 2-cyano-phenyl, or 4-methanesulfonyl-phenyl; and $Ar^2$ is phenyl, 2-methoxy-phenyl, 3-methoxy-phenyl, 4-methoxy-phenyl, 2-chloro-phenyl, 3-chloro-phenyl, 4-chloro-phenyl, 2-methyl-phenyl, 3-methyl-phenyl, 4-methyl-phenyl, 2-fluoro-phenyl, 3-fluoro-phenyl, 4-fluoro-phenyl, 2-ethoxy-phenyl, 2-acetyl-phenyl, 2,3-dimethoxy-phenyl, 2,4-dimethoxy-phenyl, 2,5-dimethoxy-phenyl, 3,4-dimethoxy-phenyl, 3,5-dimethoxy-phenyl, 3,6-dimethoxy-phenyl, 2,3-dichloro-phenyl, 2,4-dichloro-phenyl, 2,5-dichloro-phenyl, 3,4-dichloro-phenyl, 3,5-dichloro-phenyl, 3,6-dichloro-phenyl, 2,3-difluoro-phenyl, 2,4-difluoro-phenyl, 2,5-difluoro-phenyl, 3,4-difluoro-phenyl, 3,5-difluoro-phenyl, 3,6-difluoro-phenyl, 2,3-dimethyl-phenyl, 2,4-dimethyl-phenyl, 2,5-dimethyl-phenyl, 3,4-dimethyl-phenyl, 3,5-dimethyl-phenyl, 3,6-dimethyl-phenyl, 3-chloro-2-methoxy-phenyl, 4-chloro-2-methoxy-phenyl, 5-chloro-2-methoxy-phenyl, 6-chloro-2-methoxy-phenyl, 2-chloro-3-methoxy-phenyl, 4-chloro-3-methoxy-phenyl, 5-chloro-3-methoxy-phenyl, 6-chloro-3-methoxy-phenyl, 2-chloro-4-methoxy-phenyl, 2-chloro-5-methoxy-phenyl, 3-fluoro-2-methoxy-phenyl, 4-fluoro-2-methoxy-phenyl, 5-fluoro-2-methoxy-phenyl, 6-fluoro-2-methoxy-phenyl, 2-fluoro-3-methoxy-phenyl, 4-fluoro-3-methoxy-phenyl, 5-fluoro-3-methoxy-phenyl, 6-fluoro-3-methoxy-phenyl, 2-fluoro-4-methoxy-phenyl, 2-fluoro-5-methoxy-phenyl, 3-methyl-2-methoxy-phenyl, 4-methyl-2-methoxy-phenyl, 5-methyl-2-methoxy-phenyl, 6-methyl-2-methoxy-phenyl, 2-methyl-3-methoxy-phenyl, 4-methyl-3-methoxy-phenyl, 5-methyl-3-methoxy-phenyl, 6-methyl-3-methoxy-phenyl, 2-methyl-4-methoxy-phenyl, 2-methyl-5-methoxy-phenyl, 2-methanesulfanyl-phenyl, 2-hydroxy-phenyl, 4-ethoxycarbonyl-phenyl, 2-ethyl-phenyl, 2-cyano-phenyl, 4-methanesulfonyl-phenyl, 4-aminosulfonyl-phenyl, 4-dimethylamino-phenyl or 3-bromo-4-methoxy-phenyl.

In certain embodiments the invention provides compounds of formula I wherein:

n is 2 or 3;
$R^1$ is hydrogen;
$R^2$ is hydrogen;
$Ar^1$ is 2-methoxy-phenyl, 4-methoxy-phenyl, 4-chloro-phenyl, 4-methyl-phenyl, 2-methyl-phenyl, 2-chloro-phenyl, 2-fluoro-phenyl, 2-ethoxy-phenyl, 2-acetyl-phenyl, 2,4-dimethoxy-phenyl, 3,6-dimethoxy-phenyl, 5-fluoro-2-methoxy-phenyl, 5-chloro-2-methoxy-phenyl, 2,5-dichloro-phenyl, 2-hydroxymethyl-phenyl, 2,3-dichloro-phenyl, 2-methanesulfanyl-phenyl, 2,3-difluoro-phenyl, 2,4-dichloro-phenyl, 2-hydroxy-phenyl, 4-ethoxycarbonyl-phenyl, 2-ethyl-phenyl, 2-cyano-phenyl, 2,3-dimethoxy-phenyl, 4-methoxy-2-methyl-phenyl or 4-methanesulfonyl-phenyl; and
$Ar^2$ is phenyl, 3-methoxy-phenyl, 4-methoxy-phenyl, 4-aminosulfonyl-phenyl, 4-chloro-phenyl, 3,4-dichloro-phenyl, 3-bromo-4-methoxy-phenyl, 2-fluoro-phenyl, 3,4-difluoro-phenyl, 4-methyl-phenyl, 3-methyl-phenyl, 4-fluoro-phenyl, 4-dimethylamino-phenyl, 2-methyl-phenyl, 3,4-ethylenedioxy-phenyl or 4-methanesulfonylphenyl.

In certain embodiments the invention provides compounds of formula I wherein:

n is 2 or 3;
$R^1$ is hydrogen;
$R^2$ is hydrogen;
$Ar^1$ is 4-methoxy-phenyl, 4-chloro-phenyl, 4-methyl-phenyl, 2-methyl-phenyl, 2-chloro-phenyl, 2-fluoro-phenyl, 2-ethoxy-phenyl, 2-acetyl-phenyl, 2,4-dimethoxy-phenyl, 3,6-dimethoxy-phenyl, 5-fluoro-2-methoxy-phenyl, 5-chloro-2-methoxy-phenyl, 2,5-dichloro-phenyl, 2-hydroxymethyl-phenyl, 2,3-dichloro-phenyl, 2-methanesulfanyl-phenyl, 2,3-difluoro-phenyl, 2,4-dichloro-phenyl, 2-hydroxy-phenyl, 4-ethoxycarbonyl-phenyl, 2-ethyl-phenyl, 2-cyano-phenyl, 2,3-dimethoxy-phenyl, 4-methoxy-2-methyl-phenyl or 4-methanesulfonyl-phenyl; and
$Ar^2$ is phenyl, 3-methoxy-phenyl, 4-methoxy-phenyl, 3,4-dimethoxy-phenyl, 4-aminosulfonyl-phenyl, 4-chloro-phenyl, 3,4-dichloro-phenyl, 3-bromo-4-methoxy-phenyl, 2-fluoro-phenyl, 3,4-difluoro-phenyl, 4-methyl-phenyl, 3-methyl-phenyl, 4-fluoro-phenyl, 4-dimethylamino-phenyl, 2-methyl-phenyl, 3,4-ethylenedioxy-phenyl or 4-methanesulfonylphenyl.

In certain embodiments of the invention the subject compounds are of formula II:

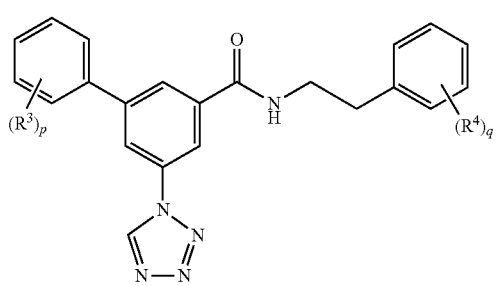

wherein:
p is from 1 to 3;
q is from 0 to 3; and
each $R^3$ and $R^4$ is independently:

halo;
C$_{1-6}$alkyl;
C$_{1-6}$alkoxy;
halo-C$_{1-6}$alkyl;
C$_{1-6}$alkyl-carbonyl;
C$_{1-6}$alkoxy-carbonyl;
C$_{1-6}$alkyl-sulfonyl;
C$_{1-6}$alkyl-sulfanyl;
amino;
hydroxy-C$_{1-6}$alkyl;
hydroxy;
cyano; or
two of R$^3$ may form alkylenedioxy; or
two of R$^4$ may form alkylenedioxy;
provided that when p is 1, q is 2 and R$^3$ is methoxy at the 2-position of the phenyl ring to which it is attached, then R$^4$ is not methoxy at the 3- and 4-positions of the phenyl ring to which they are attached.

In certain embodiments of formula II, p is from 0 to 2.

In certain embodiments of formula II, p is 1 or 2.

In certain embodiments of formula II, each R$^3$ is independently fluoro, chloro, methyl, ethyl, hydroxy, methoxy, ethoxy, acetyl, methanesulfonyl, methanesulfanyl, hydroxymethyl, ethoxycarbonyl or cyano.

In certain embodiments of formula II, q is from 0 to 2.

In certain embodiments of formula II, q is 1 or 2.

In certain embodiments of formula II, each R$^4$ is independently fluoro, chloro, bromo, methyl, methoxy, aminosulfonyl, dimethylamino, or methanesulfonyl, or two of R$^3$ may form methylenedioxy.

In certain embodiments of formula II, p is 1 and R$^3$ is methoxy.

The invention also provides a method for treating indications mediated by or associated with a nicotinic alpha 7 modulator, the method comprising administering to a subject in need thereof an effective amount of a compound of formula I

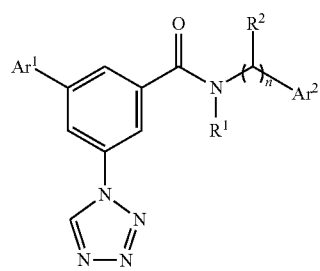

or a pharmaceutically acceptable salt thereof,
wherein:
n is from 1 to 3;
Ar$^1$ and Ar$^2$ each independently is optionally substituted phenyl or optionally substituted pyridinyl;
R$^1$ is hydrogen or C$_{1-6}$alkyl;
R$^2$ is hydrogen, or R$^2$ may form an alkylene bridge with Ar$^2$.

Where any of R$^1$, R$^2$ and R$^3$ herein are alkyl or contain an alkyl moiety, such alkyl is preferably lower alkyl, i.e. C$_1$-C$_6$alkyl, and more preferably C$_1$-C$_4$alkyl.

Representative compounds in accordance with the methods of the invention are shown in Table 1.

TABLE 1

| # | Structure | Name | M + H |
|---|-----------|------|-------|
| 1 | 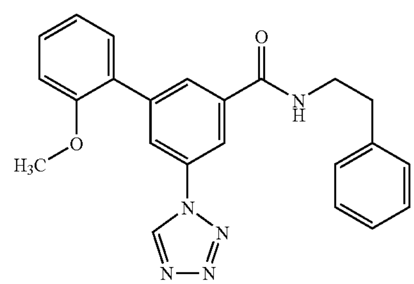 | 2'-Methoxy-5-tetrazol-1-yl-biphenyl-3-carboxylic acid phenethyl-amide | 400 |
| 2 | 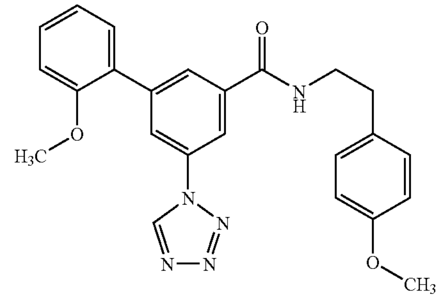 | 2'-Methoxy-5-tetrazol-1-yl-biphenyl-3-carboxylic acid [2-(4-methoxyphenyl)-ethyl]-amide | 430 |

TABLE 1-continued

| # | Structure | Name | M + H |
|---|---|---|---|
| 3 | 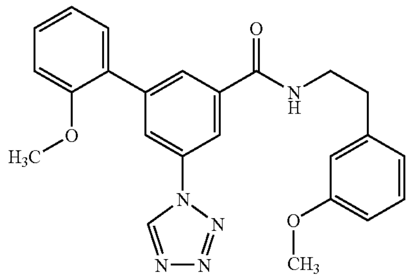 | 2'-Methoxy-5-tetrazol-1-yl-biphenyl-3-carboxylic acid [2-(3-methoxy-phenyl)-ethyl]-amide | 430 |
| 4 | 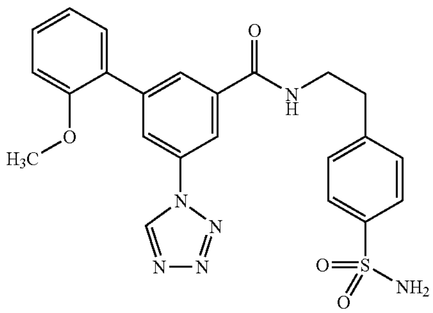 | 2'-Methoxy-5-tetrazol-1-yl-biphenyl-3-carboxylic acid [2-(4-sulfamoyl-phenyl)-ethyl]-amide | 479 |
| 5 | 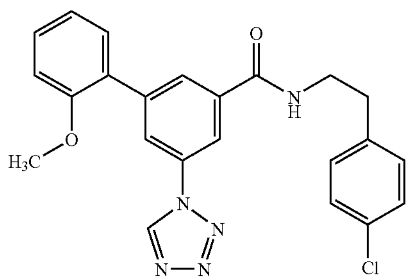 | 2'-Methoxy-5-tetrazol-1-yl-biphenyl-3-carboxylic acid [2-(4-chloro-phenyl)-ethyl]-amide | 434 |
| 6 | 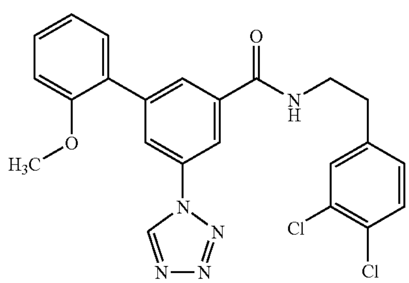 | 2'-Methoxy-5-tetrazol-1-yl-biphenyl-3-carboxylic acid [2-(3,4-dichloro-phenyl)-ethyl]-amide | 468 |
| 7 | 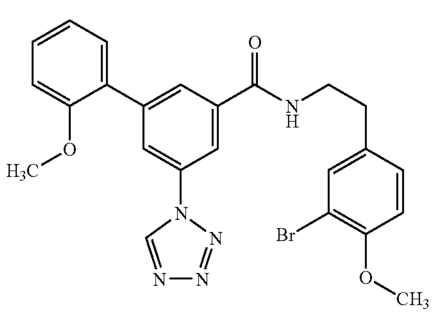 | 2'-Methoxy-5-tetrazol-1-yl-biphenyl-3-carboxylic acid [2-(3-bromo-4-methoxy-phenyl)-ethyl]-amide | 509 |

TABLE 1-continued

| # | Structure | Name | M + H |
|---|---|---|---|
| 8 | 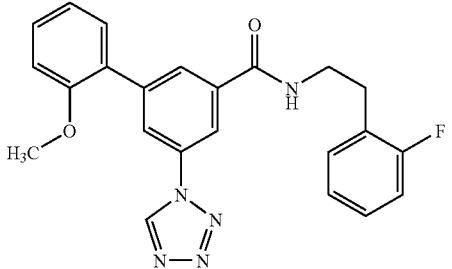 | 2'-Methoxy-5-tetrazol-1-yl-biphenyl-3-carboxylic acid [2-(2-fluoro-phenyl)-ethyl]-amide | 418 |
| 9 | 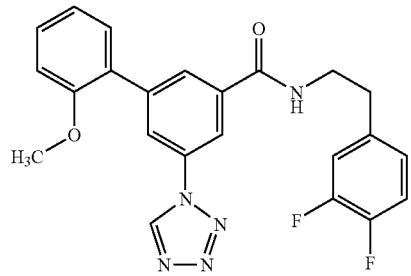 | 2'-Methoxy-5-tetrazol-1-yl-biphenyl-3-carboxylic acid [2-(3,4-difluoro-phenyl)-ethyl]-amide | 436 |
| 10 | 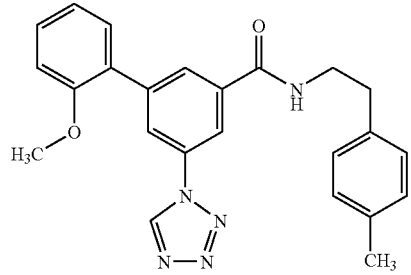 | 2'-Methoxy-5-tetrazol-1-yl-biphenyl-3-carboxylic acid (2-p-tolyl-ethyl)-amide | 414 |
| 11 | 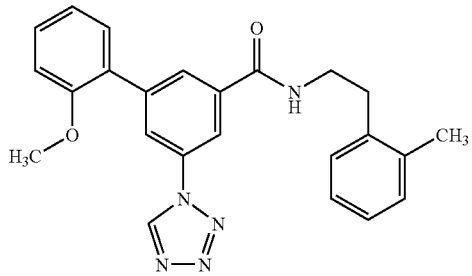 | 2'-Methoxy-5-tetrazol-1-yl-biphenyl-3-carboxylic acid (2-o-tolyl-ethyl)-amide | 414 |
| 12 | 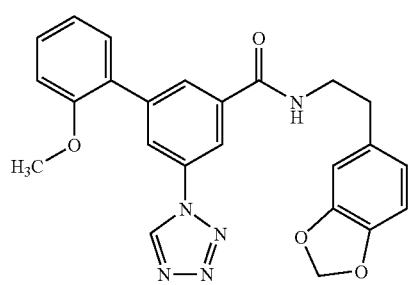 | 2'-Methoxy-5-tetrazol-1-yl-biphenyl-3-carboxylic acid (2-benzo[1,3]dioxol-5-yl-ethyl)-amide | 444 |

TABLE 1-continued

| # | Structure | Name | M + H |
|---|---|---|---|
| 13 | 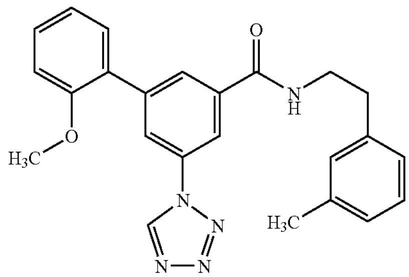 | 2'-Methoxy-5-tetrazol-1-yl-biphenyl-3-carboxylic acid (2-m-tolyl-ethyl)-amide | 414 |
| 14 | 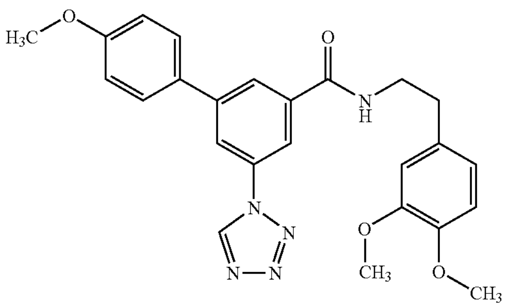 | 4'-Methoxy-5-tetrazol-1-yl-biphenyl-3-carboxylic acid [2-(3,4-dimethoxy-phenyl)-ethyl]-amide | 138.5-139.5° C. |
| 15 | 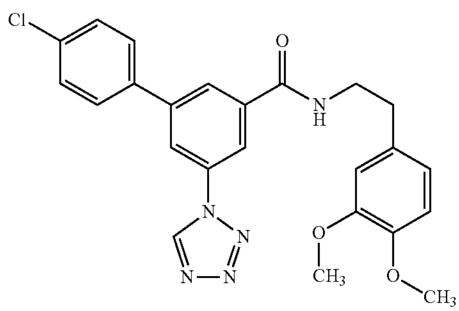 | 4'-Chloro-5-tetrazol-1-yl-biphenyl-3-carboxylic acid [2-(3,4-dimethoxy-phenyl)-ethyl]-amide | 177.8-197.4° C. |
| 16 | 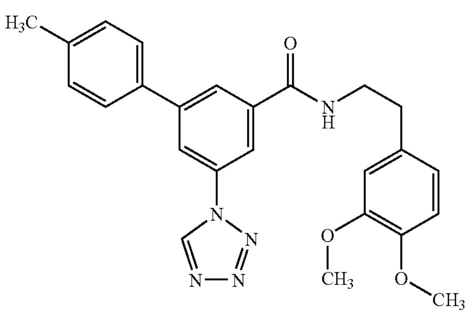 | 4'-Methyl-5-tetrazol-1-yl-biphenyl-3-carboxylic acid [2-(3,4-dimethoxy-phenyl)-ethyl]-amide | 179.2-181.1° C. |
| 17 | 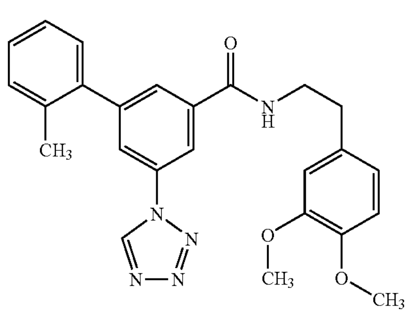 | 2'-Methyl-5-tetrazol-1-yl-biphenyl-3-carboxylic acid [2-(3,4-dimethoxy-phenyl)-ethyl]-amide | 444 |

TABLE 1-continued

| # | Structure | Name | M + H |
|---|---|---|---|
| 18 | 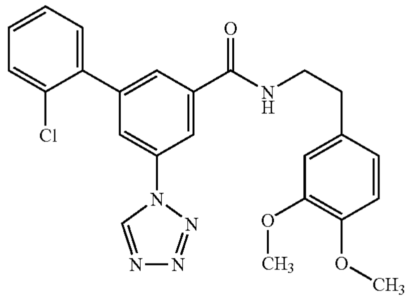 | 2'-Chloro-5-tetrazol-1-yl-biphenyl-3-carboxylic acid [2-(3,4-dimethoxy-phenyl)-ethyl]-amide | 464 |
| 19 | 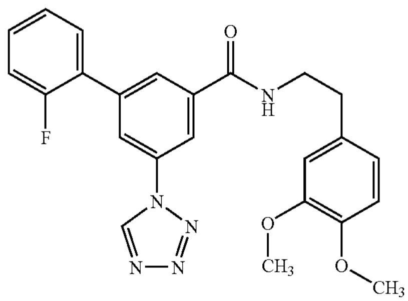 | 2'-Fluoro-5-tetrazol-1-yl-biphenyl-3-carboxylic acid [2-(3,4-dimethoxy-phenyl)-ethyl]-amide | 448 |
| 20 | 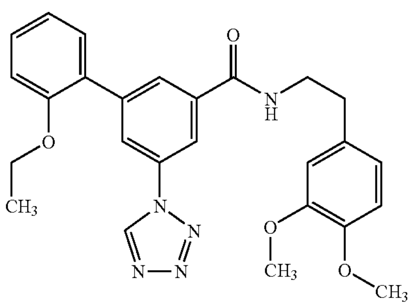 | 2'-Ethoxy-5-tetrazol-1-yl-biphenyl-3-carboxylic acid [2-(3,4-dimethoxy-phenyl)-ethyl]-amide | 474 |
| 21 | 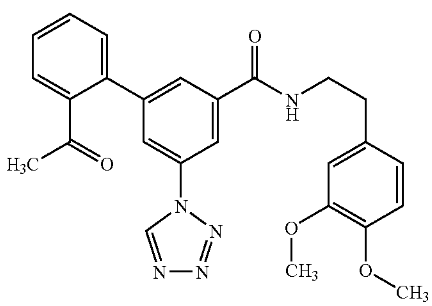 | 2'-Acetyl-5-tetrazol-1-yl-biphenyl-3-carboxylic acid [2-(3,4-dimethoxy-phenyl)-ethyl]-amide | 472 |
| 22 | 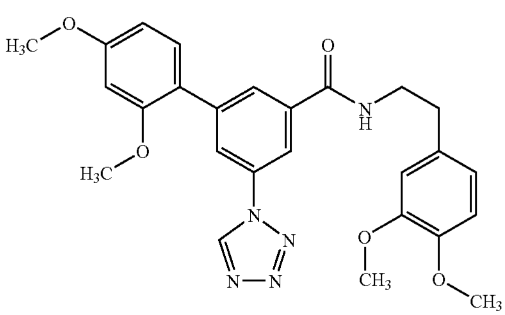 | 2',4'-Dimethoxy-5-tetrazol-1-yl-biphenyl-3-carboxylic acid [2-(3,4-dimethoxy-phenyl)-ethyl]-amide | 490 |

TABLE 1-continued

| # | Structure | Name | M + H |
|---|-----------|------|-------|
| 23 | 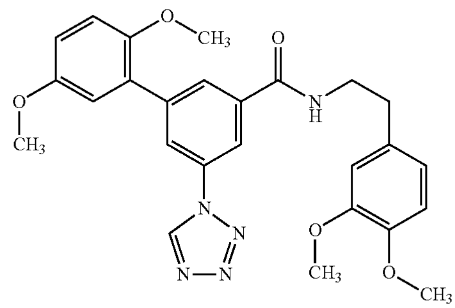 | 2',5'-Dimethoxy-5-tetrazol-1-yl-biphenyl-3-carboxylic acid [2-(3,4-dimethoxy-phenyl)-ethyl]-amide | 490 |
| 24 | 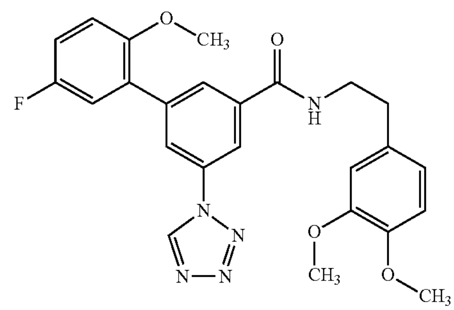 | 5'-Fluoro-2'-methoxy-5-tetrazol-1-yl-biphenyl-3-carboxylic acid [2-(3,4-dimethoxy-phenyl)-ethyl]-amide | 478 |
| 25 | 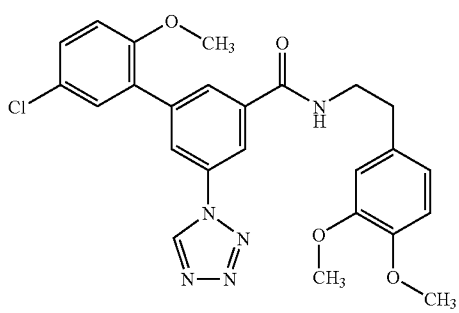 | 5'-Chloro-2'-methoxy-5-tetrazol-1-yl-biphenyl-3-carboxylic acid [2-(3,4-dimethoxy-phenyl)-ethyl]-amide | 494 |
| 26 | 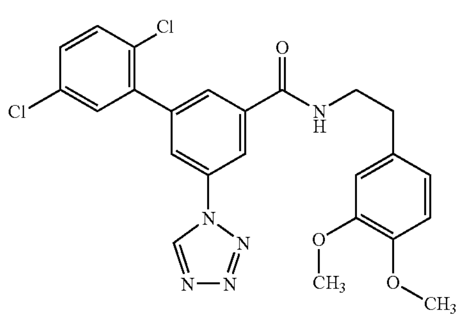 | 2',5'-Dichloro-5-tetrazol-1-yl-biphenyl-3-carboxylic acid [2-(3,4-dimethoxy-phenyl)-ethyl]-amide | 498 |
| 27 | 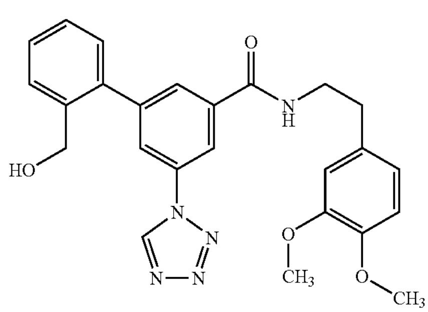 | 2'-Hydroxymethyl-5-tetrazol-1-yl-biphenyl-3-34carboxylic acid [2-(3,4-dimethoxy-phenyl)-ethyl]-amide | 460 |

TABLE 1-continued

| # | Structure | Name | M + H |
|---|---|---|---|
| 28 | 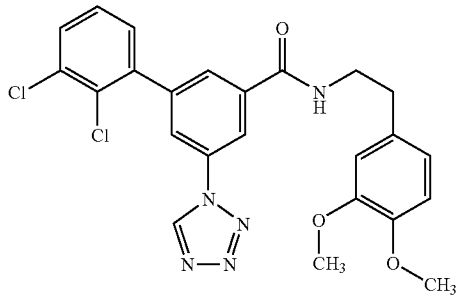 | 2',3'-Dichloro-5-tetrazol-1-yl-biphenyl-3-carboxylic acid [2-(3,4-dimethoxy-phenyl)-ethyl]-amide | 498 |
| 29 | 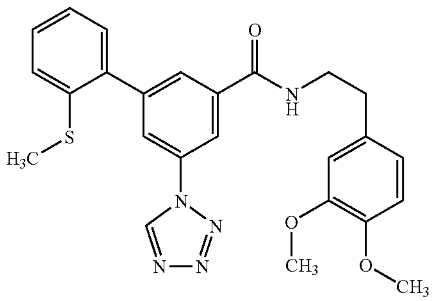 | 2'-Methylsulfanyl-5-tetrazol-1-yl-biphenyl-3-carboxylic acid [2-(3,4-dimethoxy-phenyl)-ethyl]-amide | 476 |
| 30 | 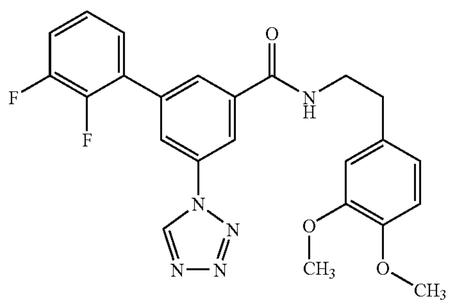 | 2',3'-Difluoro-5-tetrazol-1-yl-biphenyl-3-carboxylic acid [2-(3,4-dimethoxy-phenyl)-ethyl]-amide | 466 |
| 31 | 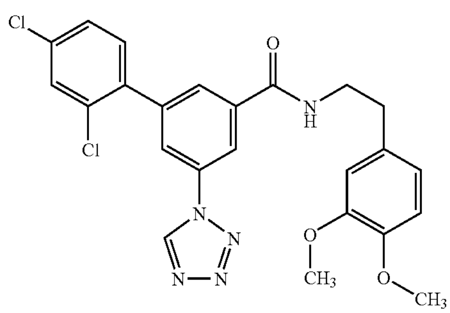 | 2',4'-Dichloro-5-tetrazol-1-yl-biphenyl-3-carboxylic acid [2-(3,4-dimethoxy-phenyl)-ethyl]-amide | 498 |
| 32 | 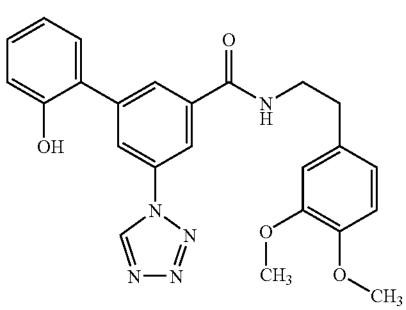 | 2'-Hydroxy-5-tetrazol-1-yl-biphenyl-3-carboxylic acid [2-(3,4-dimethoxy-phenyl)-ethyl]-amide | 446 |

TABLE 1-continued

| # | Structure | Name | M + H |
|---|---|---|---|
| 33 | 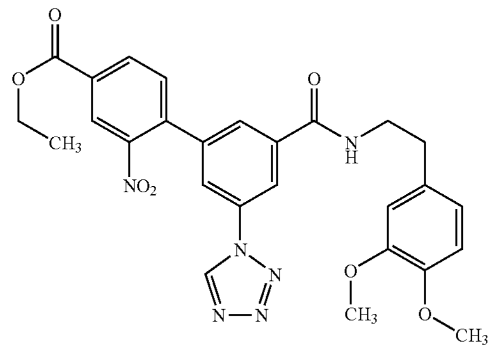 | 5'-[2-(3,4-Dimethoxy-phenyl)-ethylcarbamoyl]-2-nitro-3'-tetrazol-1-yl-biphenyl-4-carboxylic acid ethyl ester | 547 |
| 34 | 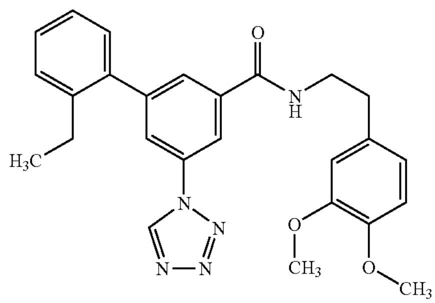 | 2'-Ethyl-5-tetrazol-1-yl-biphenyl-3-carboxylic acid [2-(3,4-dimethoxy-phenyl)-ethyl]-amide | 458 |
| 35 | 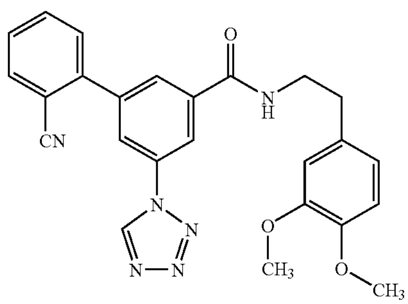 | 2'-Cyano-5-tetrazol-1-yl-biphenyl-3-carboxylic acid [2-(3,4-dimethoxy-phenyl)-ethyl]-amide | 455 |
| 36 | 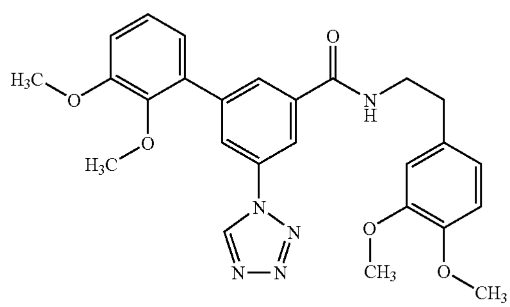 | 2',3'-Dimethoxy-5-tetrazol-1-yl-biphenyl-3-carboxylic acid [2-(3,4-dimethoxy-phenyl)-ethyl]-amide | 490 |
| 37 | 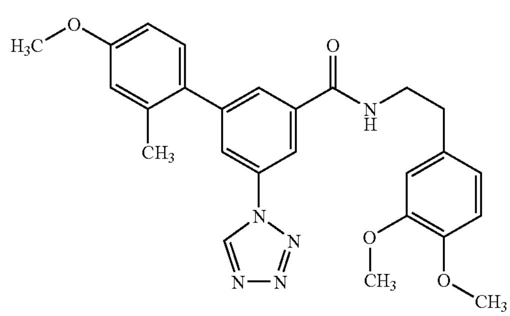 | 4'-Methoxy-2'-methyl-5-tetrazol-1-yl-biphenyl-3-carboxylic acid [2-(3,4-dimethoxy-phenyl)-ethyl]-amide | 474 |

TABLE 1-continued

| # | Structure | Name | M + H |
|---|---|---|---|
| 38 | 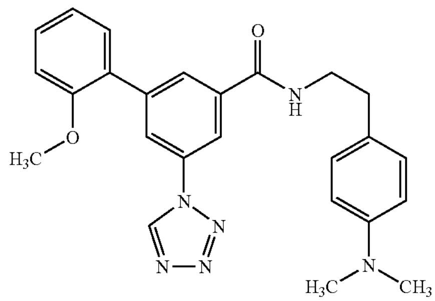 | 2'-Methoxy-5-tetrazol-1-yl-biphenyl-3-carboxylic acid [2-(4-dimethylamino-phenyl)-ethyl]-amide | 192.8-194.1° C. |
| 39 | 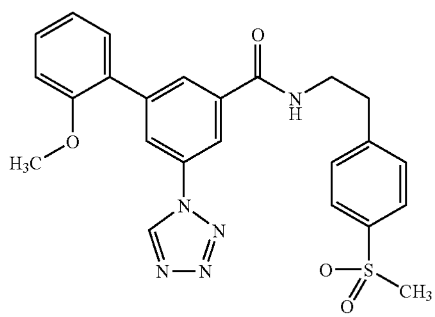 | 2'-Methoxy-5-tetrazol-1-yl-biphenyl-3-carboxylic acid [2-(4-methanesulfonyl-phenyl)-ethyl]-amide | 480 |
| 40 | 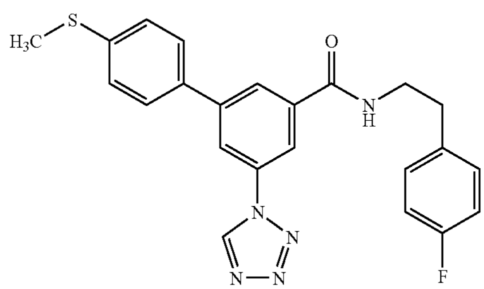 | 4'-Methylsulfanyl-5-tetrazol-1-yl-biphenyl-3-carboxylic acid [2-(2-fluoro-phenyl)-ethyl]-amide | 191.7-192.6° C. |
| 41 | 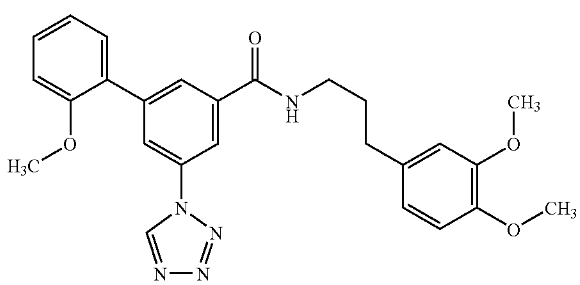 | 2'-Methoxy-5-tetrazol-1-yl-biphenyl-3-carboxylic acid [3-(3,4-dimethoxy-phenyl)-propyl]-amide | 474 |
| 42 | 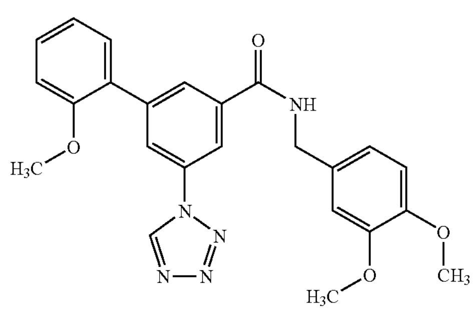 | 2'-Methoxy-5-tetrazol-1-yl-biphenyl-3-carboxylic acid 3,4-dimethoxy-benzylamide | 446 |

TABLE 1-continued

| # | Structure | Name | M + H |
|---|-----------|------|-------|
| 43 | 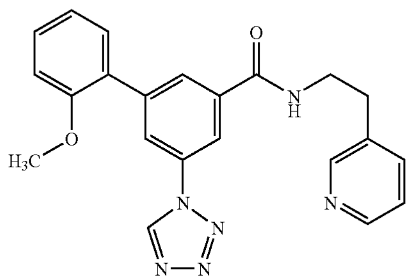 | 2'-Methoxy-5-tetrazol-1-yl-biphenyl-3-carboxylic acid (2-pyridin-3-yl-ethyl)-amide | 401 |
| 44 | 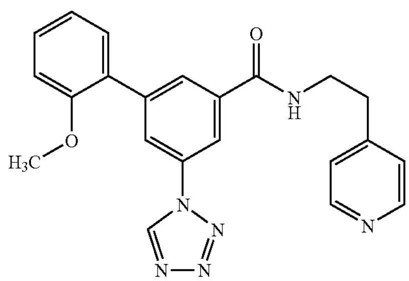 | 2'-Methoxy-5-tetrazol-1-yl-biphenyl-3-carboxylic acid (2-pyridin-4-yl-ethyl)-amide | 401 |
| 45 | 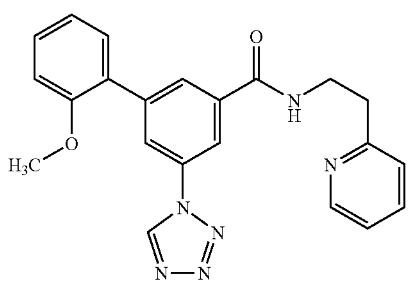 | 2'-Methoxy-5-tetrazol-1-yl-biphenyl-3-carboxylic acid (2-pyridin-2-yl-ethyl)-amide | 401 |
| 46 | 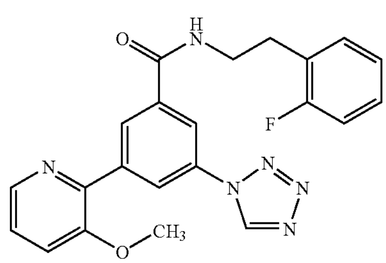 | N-[2-(2-Fluoro-phenyl)-ethyl]-3-(3-methoxy-pyridin-2-yl)-5-tetrazol-1-yl-benzamide | 419 |
| 47 | 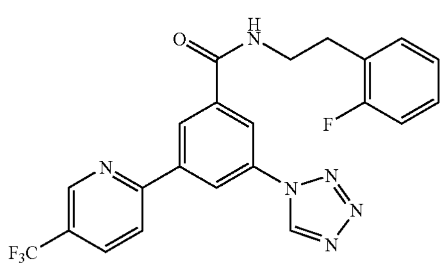 | N-[2-(2-Fluoro-phenyl)-ethyl]-3-tetrazol-1-yl-5-(5-trifluoromethyl-pyridin-2-yl)-benzamide | 457 |

TABLE 1-continued

| # | Structure | Name | M + H |
|---|-----------|------|-------|
| 48 | 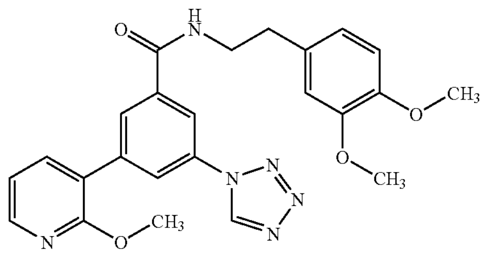 | N-[2-(3,4-Dimethoxy-phenyl)-ethyl]-3-(2-methoxy-pyridin-3-yl)-5-tetrazol-1-yl-benzamide | 461 |
| 49 | 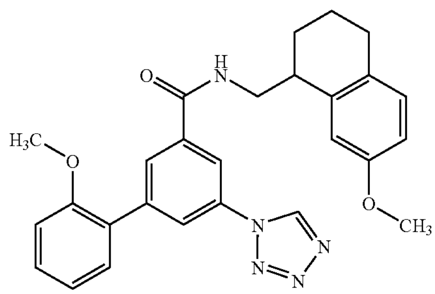 | 2'-Methoxy-5-tetrazol-1-yl-biphenyl-3-carboxylic acid (7-methoxy-1,2,3,4-tetrahydro-naphthalen-1-ylmethyl)-amide | 470 |
| 50 | 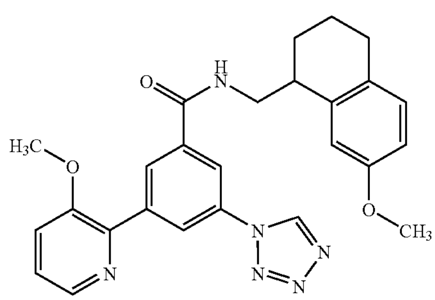 | 3-(3-Methoxy-pyridin-2-yl)-N-(7-methoxy-1,2,3,4-tetrahydro-naphthalen-1-ylmethyl)-5-tetrazol-1-yl-benzamide | 135.0-136.0° C. |
| 51 | 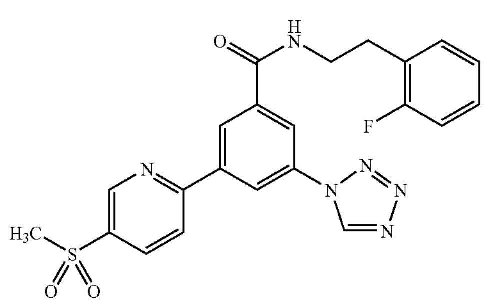 | N-[2-(2-Fluoro-phenyl)-ethyl]-3-(5-methanesulfonyl-pyridin-2-yl)-5-tetrazol-1-yl-benzamide | 467 |
| 52 | 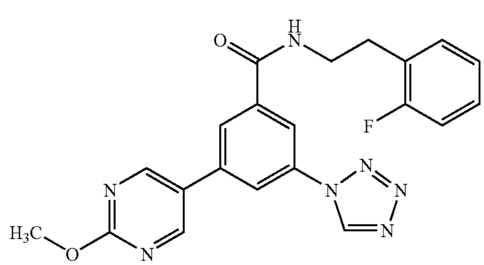 | N-[2-(2-Fluoro-phenyl)-ethyl]-3-(2-methoxy-pyrimidin-5-yl)-5-tetrazol-1-yl-benzamide | 420 |

TABLE 1-continued

| # | Structure | Name | M + H |
|---|-----------|------|-------|
| 53 | 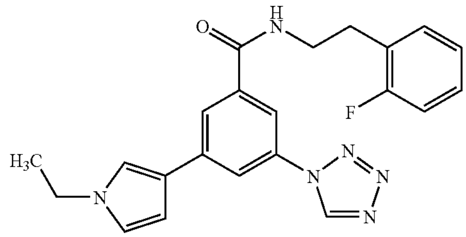 | 3-(1-Ethyl-1H-pyrrol-3-yl)-N-[2-(2-fluoro-phenyl)-ethyl]-5-tetrazol-1-yl-benzamide | 405 |
| 54 | 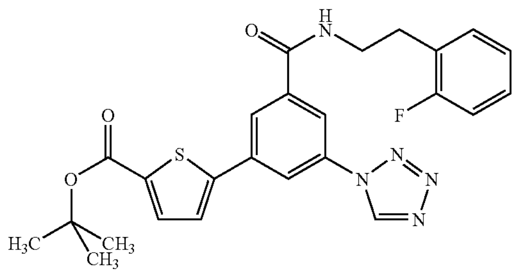 | 5-{3-[2-(2-Fluoro-phenyl)-ethylcarbamoyl]-5-tetrazol-1-yl-phenyl}-thiophene-2-carboxylic acid tert-butyl ester | 494 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein R is lower alkyl, and n, p, q, $R^3$, and $R^4$ are as defined herein.

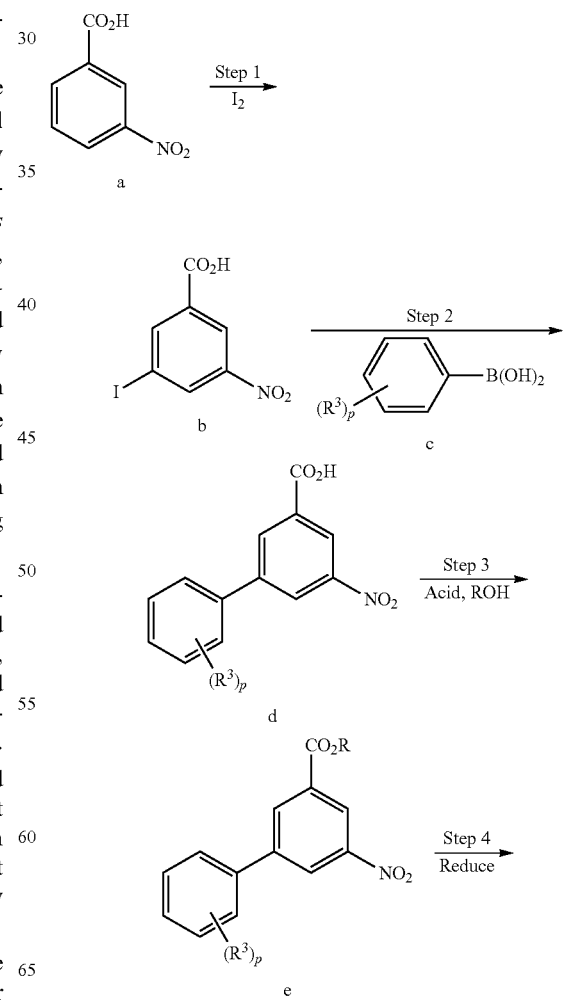

SCHEME A

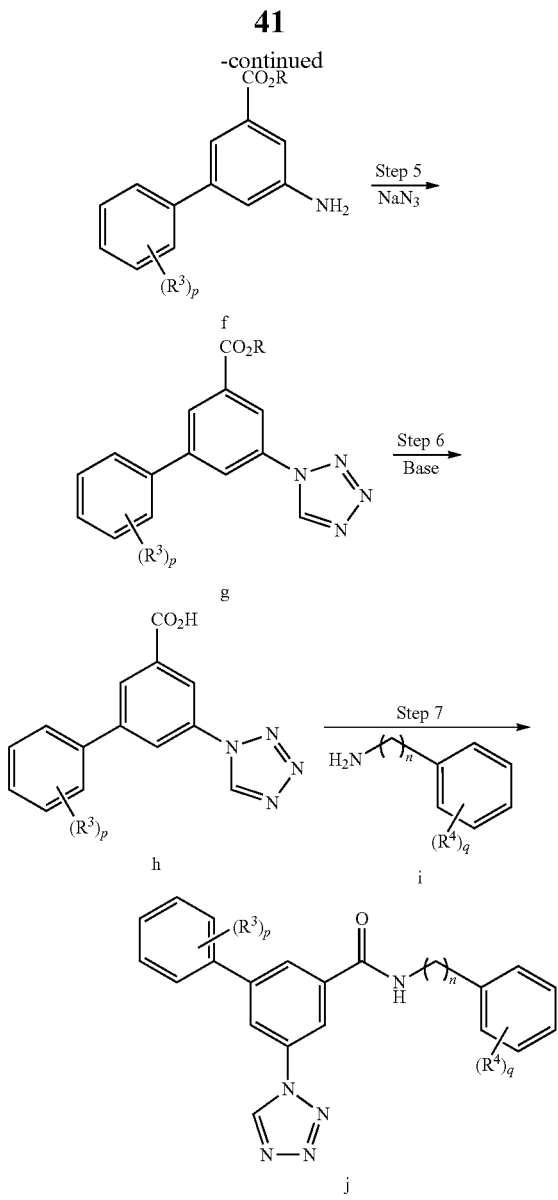

In step 1 of Scheme A, nitrobenzoic acid a undergoes iodination to afford nitro-iodobenzoic acid b. In step 2 compound b is treated with phenylboronic acid c in the presence of a suitable palladium catalyst to provide biphenyl carboxylic acid d. Compound d undergoes esterification in step 3 by reaction with lower alcohol ROH in the presence of acid to afford biphenyl carboxylic acid ester compound e. In step 4 the nitro group of compound e is reduced to an amino group to afford biphenyl amine compound f. Compound f is reacted with sodium azide in step 5 to give biphenyl tetrazole compound g. Hydrolysis of the carboxylate ester group of compound g in step 6 affords biphenyl carboxylic acid compound h. In step 7, an amide coupling reaction is carried out by reaction of carboxylic acid compound h with amine compound i, to afford biphenyl tetrazole amide compound i, which is a compound of formula I in accordance with the invention.

Many variations on the procedure of Scheme A are possible and will suggest themselves to those skilled in the art. For example, the iodine used in step 1 may be replaced with bromine in certain embodiments. Reduction of the nitro group to an amino group may be carried out on compound b prior to the Buchwald reaction of step 2. Details of the procedure of Scheme A are provided in the Experimental section below.

Utility

The compounds of the invention are usable for the treatment of diseases or conditions associated with the nicotinic alpha 7 (α7nACh) receptor, including treatment of psychotic diseases, neurodegenerative diseases, and cognitive impairments involving a dysfunction of the cholinergic system, and conditions of memory and/or cognition impairment, including, for example, schizophrenia, anxiety, mania, depression, manic depression, Tourette's syndrome, Parkinson's disease, Huntington's disease, cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder), and other uses such as treatment of nicotine addiction, inducing smoking cessation, treating pain (i.e., analgesic use), providing neuroprotection, and treating jetlag. The compounds of the invention are useful for enhancing cognition in Alzheimer's patients and patients having cognition impairment or cognitive disorders associated with schizophrenia, anxiety, mania, depression, manic depression, Tourette's syndrome, Parkinson's disease, Huntington's disease, Lewy Body Dementia, Amyotrophic Lateral Sclerosis, memory impairment, memory loss, cognition deficit, attention deficit or Attention Deficit Hyperactivity Disorder.

Thus, the invention provides a method of treating a patient or subject, specifically a mammal and especially a human, suffering from psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], and/or cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder) comprising administering to the patient an effective amount of a compound of the invention.

Neurodegenerative disorders include, but are not limited to, treatment and/or prophylaxis of Alzheimer's diseases, Pick's disease, diffuse Lewy Body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy, spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Sträussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, the compounds of the invention may be used to treat age-related dementia and other dementias and conditions with memory loss including age-related memory loss, senility, vascular dementia, diffuse white matter disease (Binswanger's disease), dementia of endocrine or metabolic origin, dementia of head trauma and diffuse brain damage, dementia pugilistica and frontal lobe dementia. Thus, the invention provides a method of treating a patient, especially a human, suffering from age-related dementia and other dementias and conditions with memory loss, as well as enhancing cognitive memory in Alzheimer's patients, comprising administering to the patient an effective amount of a compound of the invention.

The invention provides methods of treating subjects suffering from memory impairment due to, for example, Alzheimer's disease, mild cognitive impairment due to aging, schizophrenia, Parkinson's disease, Huntington's disease, Pick's disease, Creutzfeldt-Jakob disease, depression, aging, head trauma, stroke, CNS hypoxia, cerebral senility, multiinfarct dementia and other neurological conditions, as well as HIV and cardiovascular diseases, comprising administering an effective amount of a compound of the invention.

Amyloid precursor protein (APP) and Aβ peptides derived therefrom, e.g., $A\beta_{1-40}$, $A\beta_{1-2}$, and other fragments, are known to be involved in the pathology of Alzheimer's disease. The $A\beta_{1-42}$ peptides are not only implicated in neurotoxicity but also are known to inhibit cholinergic transmitter function. Further, it has been determined that Aβ peptides bind to α7nAch receptors. Agents which block the binding of the Aβ peptides to α-7 nAChRs are thus useful for treating neurodegenerative diseases. In addition, stimulation α7nACh receptors can protect neurons against cytotoxicity associated with Aβ peptides. Thus, the invention provides a method of treating and/or preventing dementia in an Alzheimer's patient which comprises administering to the subject a therapeutically effective amount of a compound according to Formulas I-IV to inhibit the binding of an amyloid beta peptide (preferably, $A\beta_{1-42}$) with nACh receptors, preferable α7nACh receptors, most preferably, human α7nACh receptors (as well as a method for treating and/or preventing other clinical manifestations of Alzheimer's disease that include, but are not limited to, cognitive and language deficits, apraxias, depression, delusions and other neuropsychiatric symptoms and signs, and movement and gait abnormalities).

The invention also provides methods for treating other amyloidosis diseases, for example, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis anthropathy, and Finnish and Iowa amyloidosis.

Nicotinic receptors have been implicated as playing a role in the body's response to alcohol ingestion, and the compounds of the invention are useful in the treatment of alcohol withdrawal and in anti-intoxication therapy.

Agonists for the α7nACh receptor subtypes can also be used for neuroprotection against damage associated with strokes and ischemia and glutamate-induced excitotoxicity, and the invention thus provides a method of treating a patient to provide for neuroprotection against damage associated with strokes and ischemia and glutamate-induced excitotoxicity comprising administering to the patient an effective amount of a compound of the invention.

Agonists for the α7nACh receptor subtypes can also be used in the treatment of nicotine addiction, inducing smoking cessation, treating pain, and treating jetlag, obesity, diabetes, and inflammation, and the invention thus provides a method of treating a patient suffering from nicotine addiction, pain, jetlag, obesity, diabetes, and/or inflammation, or a method of inducing smoking cessation in a patient comprising administering to the patient an effective amount of a compound of the invention The inflammatory reflex is an autonomic nervous system response to an inflammatory signal. Upon sensing an inflammatory stimulus, the autonomic nervous system responds through the vagus nerve by releasing acetylcholine and activating nicotinic α7 receptors on macrophages. These macrophages in turn release cytokines. Dysfunctions in this pathway have been linked to human inflammatory diseases including rheumatoid arthritis, diabetes and sepsis. Macrophages express the nicotinic α7 receptor and it is likely this receptor that mediates the cholinergic anti-inflammatory response. Therefore, compounds of the invention may be useful for treating a patient (e.g., a mammal, such as a human) suffering from an inflammatory disease or disorder, such as, but not limited to, rheumatoid arthritis, diabetes or sepsis.

The compounds of the invention are expected to find utility as analgesics in the treatment of diseases and conditions associated with pain from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Further, compounds of the invention are useful for treating respiratory disorders, including chronic obstructive pulmonary disorder (COPD), asthma, bronchospasm, and the like.

In addition, due to their affinity to α7nACh receptors, labeled derivatives of the compounds of Formulas I-IV (e.g., $C^{11}$ or $F^{18}$ labeled derivatives), can be used in neuroimaging of the receptors within, e.g., the brain. Thus, using such labeled agents in vivo imaging of the receptors can be performed using, e.g., PET imaging.

The invention also provides a method of treating a patient suffering from, for example, mild cognitive impairment (MCI), vascular dementia (VaD), age-associated cognitive decline (AACD), amnesia associated w/open-heart-surgery, cardiac arrest, and/or general anesthesia, memory deficits from early exposure of anesthetic agents, sleep deprivation induced cognitive impairment, chronic fatigue syndrome, narcolepsy, AIDS-related dementia, epilepsy-related cognitive impairment, Down's syndrome, Alcoholism related dementia, drug/substance induced memory impairments, Dementia Puglistica (Boxer Syndrome), and animal dementia (e.g., dogs, cats, horses, etc.) comprising administering to the patient an effective amount of a compound of the invention.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

| ABBREVIATIONS | |
|---|---|
| CDI | 1,1-carbonyl-diimidazole |
| DCM | dichloromethane/methylene chloride |
| DMF | N,N-dimethylformamide |
| DMAP | 4-dimethylaminopyridine |
| EDCI | 1-ethyl-3-(3'-dimethylaminopropyl)carbodiimide |
| EtOAc | ethyl acetate |
| EtOH | ethanol |
| tBuOH | tert-butanol |
| gc | gas chromatography |
| HMPA | hexamethylphosphoramide |
| HOAc | acetic acid |
| HOBt | N-Hydroxybenzotriazole |
| hplc | high performance liquid chromatography |
| mCPBA | m-chloroperbenzoic acid |
| MeCN | acetonitrile |
| MeOH | methanol |
| NMP | N-methyl pyrrolidinone |
| TEA | triethylamine |
| TFA | trifluoroacetic acid |
| THF | tetrahydrofuran |
| LDA | lithium diisopropylamine |
| LHMDS | Lithium bis(trimethylsilyl)amide |
| TBAF | tetrabutylammonium fluoride |
| TLC | thin layer chromatography |

Preparation 1

2'-Methoxy-5-tetrazol-1-yl-biphenyl-3-carboxylic acid methyl ester

The synthetic procedure described in this Preparation was carried out according to the process shown in Scheme C.

SCHEME C

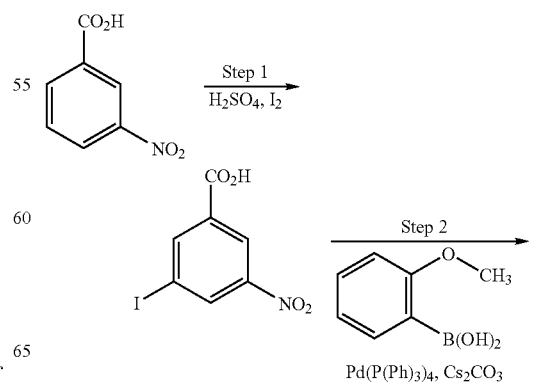

-continued

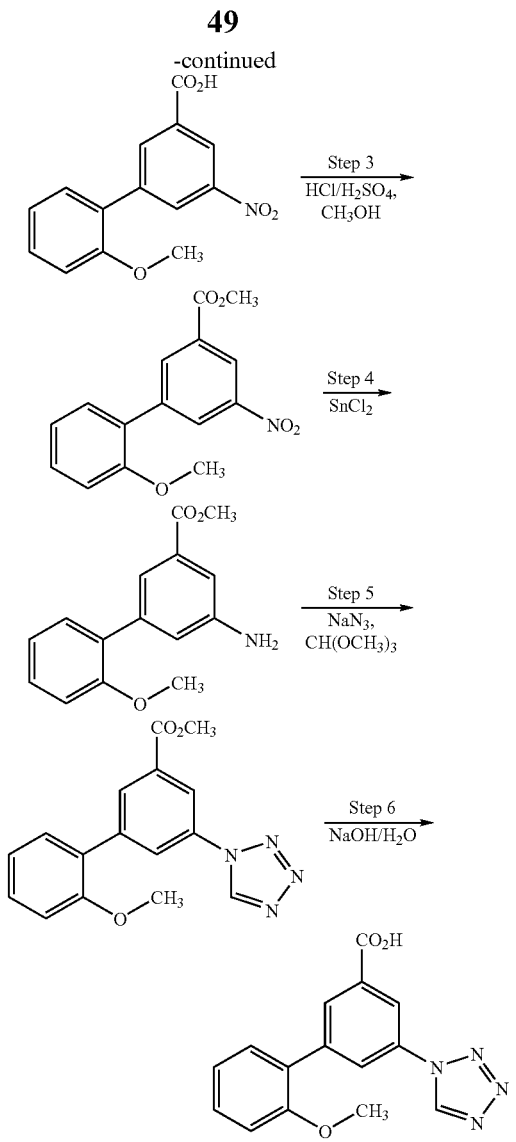

Step 1 3-Iodo-5-nitro-benzoic acid

To a mixture of 3-Nitro-benzoic acid (114 g, 0.68 mol) and I$_2$ (138.2 g) was added dropwise H$_2$SO$_4$ (conc., 230 mL). The reaction mixture was stirred at 85° C. for 18 hours, then was cooled and poured onto ice. The resulting mixture was partitioned between EtOAc and saturated aqueous NaHSO$_3$. The combined organic layers were washed with water, dried over Na$_2$SO$_4$, filtered and concentrated under reduced pressure to give 108 g of 3-iodo-5-nitro-benzoic acid as a pale yellow solid, MS (M+H)=294.

Step 2 2'-Methoxy-5-nitro-biphenyl-3-carboxylic acid

3-Iodo-5-nitro-benzoic acid (10.0 g, 34 mmol) was dissolved in 17.5 mL warm EtOH. Toluene (17.5 mL) was added, followed by 2-methoxy-phenyl-boronic acid (5.7 g), Palladium tetra(triphenylphosphine) (1.26 g) and aqueous Cs$_2$CO$_3$ solution (12.23 g in 12.5 mL H$_2$O). The reaction mixture was stirred under Argon atmosphere at 130° C. for 18 hours, then cooled to room temperature. Solvent was removed under reduced pressure, and the residue was partitioned between aqueous 1N HCl and EtOAc. The combined organic layers were washed with water, dried over Na$_2$SO$_4$, filtered and concentrated under reduced pressure. The resulting solid residue was added to a mixture of methylene chloride (50 mL) and hexanes (10 mL) and stirred for two hours. The mixture was filtered, and the resulting white solid was washed with cold methylene chloride/hexanes (5:1) and dried to give 8.62 g of 2'-methoxy-5-nitro-biphenyl-3-carboxylic acid, MS (M+H)=274.

Step 3 2'-Methoxy-5-nitro-biphenyl-3-carboxylic acid methyl ester

2'-Methoxy-5-nitro-biphenyl-3-carboxylic acid (8.62 g, 31.5 mmol) was added to a mixture of MeOH (89 mL) and conc. aqueous HCl (4.9 mL). The reaction mixture was stirred at 80° C. for 24 hours, and then stirred for 18 hours at room temperature. The reaction mixture was filtered, and the resulting solid was washed with MeOH and dried to give 8.2 g of 2'-methoxy-5-nitro-biphenyl-3-carboxylic acid methyl ester, MS (M+H)=288.

Step 4 5-Amino-2'-methoxy-biphenyl-3-carboxylic acid methyl ester

2'-Methoxy-5-nitro-biphenyl-3-carboxylic acid methyl ester (8.2 g, 28.5 mmol) and SnCl$_2$ dihydrate (35 g) in EtOAc (300 mL) was heated to reflux and stirred for 18 hours, then cooled and stirred at room temperature for 48 hours. Saturated aqueous NaHCO$_3$ was added until the aqueous portion of the mixture reached pH 10. The organic layer was separated, and the aqueous layer was washed with EtOAc. The combined organic layers were washed with water, dried over Na$_2$SO$_4$, filtered and concentrated under reduced pressure to give 7.2 g of 5-amino-2'-methoxy-biphenyl-3-carboxylic acid methyl ester, MS (M+H)=258.

Step 5 2'-Methoxy-5-tetrazol-1-yl-biphenyl-3-carboxylic acid methyl ester

To a suspension of 5-amino-2'-methoxy-biphenyl-3-carboxylic acid methyl ester (7.2 g, 28 mmol) in trimethoxymethane (22.8 mL) was added NaN$_3$ (5.7 g) followed by HOAc (285 mL). The reaction mixture was stirred at room temperature for 30 minutes, then stirred at 100° C. for three hours, and then stirred at room temperature for 18 hours. The resulting mixture was partitioned between water and methylene chloride, and the combined organic layers were washed with water, dried over Na$_2$SO$_4$, filtered and concentrated under reduced pressure to give 8.6 g of 2'-methoxy-5-tetrazol-1-yl-biphenyl-3-carboxylic acid methyl ester, MS (M+H)=311.

Step 6 2'-Methoxy-5-tetrazol-1-yl-biphenyl-3-carboxylic acid

A mixture of 2'-methoxy-5-tetrazol-1-yl-biphenyl-3-carboxylic acid methyl ester (8.6 g, 27.7 mmol), 3N aqueous NaOH (28.5 mL) and MeOH (28.5 mL) was stirred at room temperature for 18 hours. The reaction mixture was filtered and the collected solid was partitioned between 1N aqueous HCl and methylene chloride. A white precipitate formed in the methylene chloride layer and was collected by filtration, washed with water and methylene chloride, and dried to give 4.2 g (46%) of 2'-methoxy-5-tetrazol-1-yl-biphenyl-3-carboxylic acid, MP=214.0-215.3° C., MS (M+H)=297.

Similarly prepared, but replacing 2-methoxy-phenyl-boronic acid with 4-methoxy-phenyl-boronic acid, was 4'-methoxy-5-tetrazol-1-yl-biphenyl-3-carboxylic acid, MS (M+H)= 297.

Similarly prepared, but replacing 2-methoxy-phenyl-boronic acid with 4-chloro-phenyl-boronic acid, was 4'-chloro-5-tetrazol-1-yl-biphenyl-3-carboxylic acid, MS (M+H)=301.

Similarly prepared, but replacing 2-methoxy-phenyl-boronic acid with 4-methyl-phenyl-boronic acid, was 4'-methyl-5-tetrazol-1-yl-biphenyl-3-carboxylic acid, MS (M+H)= 281.

Similarly prepared, but replacing 2-methoxy-phenyl-boronic acid with 2-methyl-phenyl-boronic acid, was 2'-methyl-5-tetrazol-1-yl-biphenyl-3-carboxylic acid, MS (M+H) =281.

Similarly prepared, but replacing 2-methoxy-phenyl-boronic acid with 2-chloro-phenyl-boronic acid, was 2'-chloro-5-tetrazol-1-yl-biphenyl-3-carboxylic acid, MS (M+H)=301.

Similarly prepared, but replacing 2-methoxy-phenyl-boronic acid with 2-fluoro-phenyl-boronic acid, was 2'-fluoro-5-tetrazol-1-yl-biphenyl-3-carboxylic acid, MS (M+H)=285.

Similarly prepared, but replacing 2-methoxy-phenyl-boronic acid with 2-ethoxy-phenyl-boronic acid, was 2'-ethoxy-5-tetrazol-1-yl-biphenyl-3-carboxylic acid, MS (M+H)=311.

Similarly prepared, but replacing 2-methoxy-phenyl-boronic acid with 2-acetyl-phenyl-boronic acid, was 2'-acetyl-5-tetrazol-1-yl-biphenyl-3-carboxylic acid, MS (M+H)=309.

Similarly prepared, but replacing 2-methoxy-phenyl-boronic acid with 2,4-dimethoxy-phenyl-boronic acid, was 2',4'-dimethoxy-5-tetrazol-1-yl-biphenyl-3-carboxylic acid, MS (M+H)=327.

Similarly prepared, but replacing 2-methoxy-phenyl-boronic acid with 2,5-dimethoxy-phenyl-boronic acid, was 2',5'-dimethoxy-5-tetrazol-1-yl-biphenyl-3-carboxylic acid, MS (M+H)=327.

Similarly prepared, but replacing 2-methoxy-phenyl-boronic acid with 5-fluoro-2-methoxy-phenyl-boronic acid, was 5'-fluoro-2'-methoxy-5-tetrazol-1-yl-biphenyl-3-carboxylic acid, MS (M+H)=315.

Similarly prepared, but replacing 2-methoxy-phenyl-boronic acid with 5-chloro-2-methoxy-phenyl-boronic acid, was 5'-chloro-2'-methoxy-5-tetrazol-1-yl-biphenyl-3-carboxylic acid, MS (M+H)=331.

Similarly prepared, but replacing 2-methoxy-phenyl-boronic acid with 2,5-dichloro-phenyl-boronic acid, was 2',5'-dichloro-5-tetrazol-1-yl-biphenyl-3-carboxylic acid, MS (M+H)=335.

Similarly prepared, but replacing 2-methoxy-phenyl-boronic acid with 2,3-dichloro-phenyl-boronic acid, was 2',3'-dichloro-5-tetrazol-1-yl-biphenyl-3-carboxylic acid, MS (M+H)=335.

Similarly prepared, but replacing 2-methoxy-phenyl-boronic acid with 2-hydroxymethyl-phenyl-boronic acid, was 2'-hydroxymethyl-5-tetrazol-1-yl-biphenyl-3-carboxylic acid, MS (M+H)=297.

Similarly prepared, but replacing 2-methoxy-phenyl-boronic acid with 2-methanesulfanyl-phenyl-boronic acid, was 2'-methanesulfanyl-5-tetrazol-1-yl-biphenyl-3-carboxylic acid, MS (M+H)=313.

Similarly prepared, but replacing 2-methoxy-phenyl-boronic acid with 2,3-difluoro-phenyl-boronic acid, was 2',3'-difluoro-5-tetrazol-1-yl-biphenyl-3-carboxylic acid, MS (M+H)=303.

Similarly prepared, but replacing 2-methoxy-phenyl-boronic acid with 2,4-dichloro-phenyl-boronic acid, was 2',4'-dichloro-5-tetrazol-1-yl-biphenyl-3-carboxylic acid, MS (M+H)=335.

Similarly prepared, but replacing 2-methoxy-phenyl-boronic acid with 2-ethyl-phenyl-boronic acid, was 2'-ethyl-5-tetrazol-1-yl-biphenyl-3-carboxylic acid, MS (M+H)=295.

Similarly prepared, but replacing 2-methoxy-phenyl-boronic acid with 2-cyano-phenyl-boronic acid, was 2'-cyano-5-tetrazol-1-yl-biphenyl-3-carboxylic acid, MS (M+H)=292.

Similarly prepared, but replacing 2-methoxy-phenyl-boronic acid with 2,3-dimethoxy-phenyl-boronic acid, was 2',3'-dimethoxy-5-tetrazol-1-yl-biphenyl-3-carboxylic acid, 327.

Similarly prepared, but replacing 2-methoxy-phenyl-boronic acid with 4-methoxy-2-methyl-phenyl-boronic acid, was 4'-methoxy-2'-methyl-5-tetrazol-1-yl-biphenyl-3-carboxylic acid, MS (M+H)=311.

Preparation 2

3-(3-Methoxy-pyridin-2-yl)-5-tetrazol-1-yl-benzoic acid

The synthetic procedure described in this Preparation was carried out according to the process shown in Scheme D.

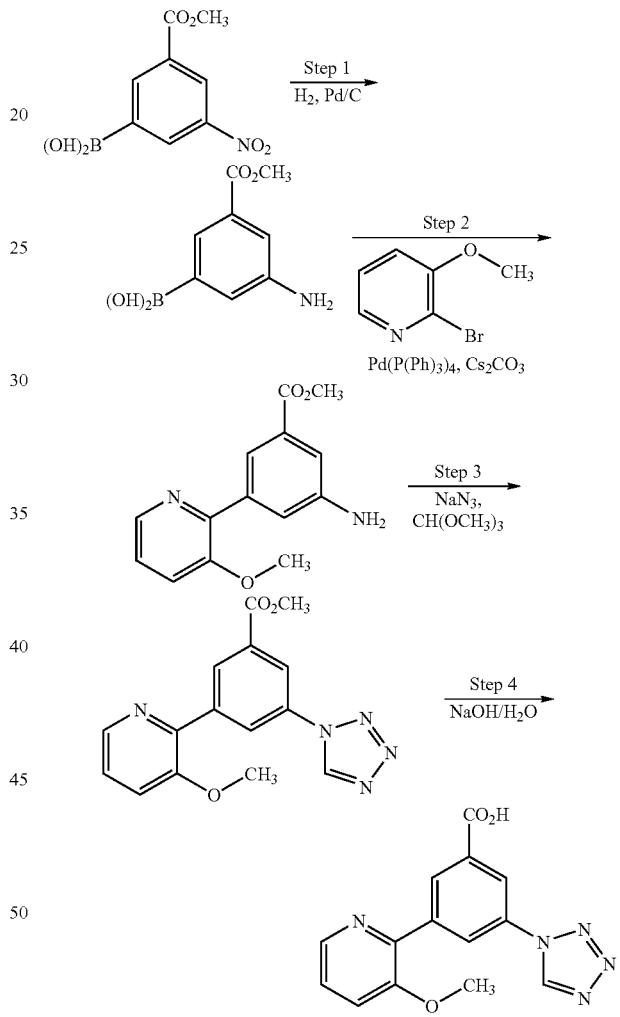

Step 1 3-Amino-5-boronyl-benzoic acid methyl ester 3-boronyl-5-nitro-benzoic acid methyl ester (11.6 g, 51.1 mmol) and 10% Pd/C (1.05 g) were added to 110 mL EtOH in a one liter Parr vessel. The reaction mixture was shaken under 42 psi (2.9 Bar) for 20 minutes. The reaction mixture was purged with nitrogen and filtered through $Na_2SO_4$ and Celite. The filtrate was concentrated under reduced pressure to give 9.89 g of 3-amino-5-boronyl-benzoic acid methyl ester.

Step 2 3-Amino-5-(3-methoxy-pyridin-2-yl)-benzoic acid methyl ester 3-amino-5-boronyl-benzoic acid methyl ester (7.6 g. 34 mmol), 2-bromo-3-methoxy-pyridine (5.8 g, 30.9 mmol), palladium tetra(triphenylphosphine) (3.6 g, 3.1 mmol), and Cs$_2$CO$_3$ (25.3 g, 77.5 mmol) were added to a mixture of EtOH (30 mL) and water (60 mL). The reaction mixture was vacuum-purged and then stirred at 90° C. for 44 hours. The reaction mixture was cooled and partitioned between water and ETOAc. The combined organic layers were washed with water, dried over Na$_2$SO$_4$, filtered and concentrated under reduced pressure. The residue was transferred onto Celite, which was then loaded onto a column of 200 g silica and eluted with EtOAc/hexanes (5%-100%) to give 530 mg of 3-amino-5-(3-methoxy-pyridin-2-yl)-benzoic acid methyl ester, MS (M+H)=259.

Step 3 3-(3-Methoxy-pyridin-2-yl)-5-tetrazol-1-yl-benzoic acid methyl ester

A suspension of 3-amino-5-(3-methoxy-pyridin-2-yl)-benzoic acid methyl ester (530 mg, 1.96 mmol) in tri-methoxymethane (1.5 mL) was stirred under nitrogen for 5 minutes. NaN$_3$ (390 mg, 5.9 mmol) was added slowly, followed by HOAc (10 mL). The reaction mixture was stirred at room temperature for 72 hours, then was concentrated under reduced pressure. The residue was partitioned between water and EtOAc. The combined organic layers were washed with water, dried over Na$_2$SO$_4$, filtered and concentrated under reduced pressure. The residue was purified via flash chromatography through 80 g of silica using EtOAc/hexanes (20%-100%) to give 170 mg of 3-(3-methoxy-pyridin-2-yl)-5-tetrazol-1-yl-benzoic acid methyl ester, MS (M+H)=312.

Step 4 3-(3-Methoxy-pyridin-2-yl)-5-tetrazol-1-yl-benzoic acid 3-(3-Methoxy-pyridin-2-yl)-5-tetrazol-1-yl-benzoic acid methyl ester (170 mg, 0.52 mmol) was added to a mixture of THF (20 mL) and MeOH (5 mL) and cooled to ice bath temperature under nitrogen atmosphere. LiOH.H$_2$O (8.8 g, 2.1 mmol) was added, and the reaction mixture was stirred for 18 hours at room temperature. The reaction mixture was concentrated under reduced pressure and 10.0 g of water ice and 10 mL of 10% aqueous HOAc were added to the residue. The resulting mixture was filtered, and the filtrate was washed with 10% aqueous HOAc. The collected solid was dried under vacuum at 60° C. for 3 horus to give 140 mg of 3-(3-methoxy-pyridin-2-yl)-5-tetrazol-1-yl-benzoic acid, MS (M+H)=298.

Similarly prepared, but replacing 2-bromo-3-methoxy-pyridine with 2-bromo-5-trifluoromethyl-pyridine in step 2, was 3-tetrazol-1-yl-5-(5-trifluoromethyl-pyridin-2-yl)-benzoic acid, MS (M+H)=336.

Similarly prepared, but replacing 2-bromo-3-methoxy-pyridine with 2-bromo-5-methanesulfonyl-pyridine in step 2, was 3-tetrazol-1-yl-5-(5-methanesulfonyl-pyridin-2-yl)-benzoic acid, MS (M+H)=316.

Similarly prepared, but replacing 2-bromo-3-methoxy-pyridine with 2-methoxy-5-bromo-pyrimidine in step 2, was 3-tetrazol-1-yl-5-(2-methoxy-pyrimidin-5-yl)-benzoic acid, MS (M+H)=269.

Similarly prepared, but replacing 2-bromo-3-methoxy-pyridine with 3-bromo-1-ethyl-pyrrol in step 2, was 3-tetrazol-1-yl-5-(1-ethyl-pyrrol-3-yl)-benzoic acid, MS (M+H)=254.

Similarly prepared, but replacing 2-bromo-3-methoxy-pyridine with thiophene-2-carboxylic acid tert-butyl ester in step 2, was 5-(3-carboxy-5-tetrazol-1-yl-phenyl)-thiophene-2-carboxylic acid tert-butyl ester, MS (M+H)=373

Example 1

2'-Methoxy-5-tetrazol-1-yl-biphenyl-3-carboxylic acid[2-(3-methoxy-phenyl)-ethyl]-amide The synthetic procedure described in this Example was carried out according to the process shown in Scheme E.

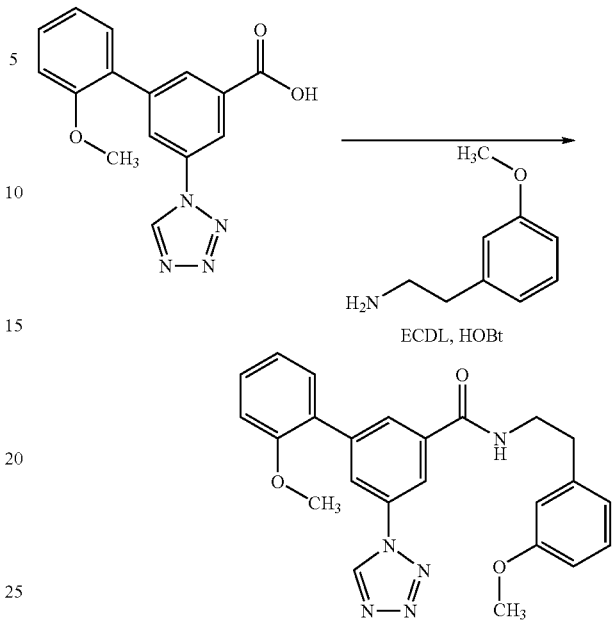

SCHEME E

2'-Methoxy-5-tetrazol-1-yl-biphenyl-3-carboxylic acid 0.9 g, 3 mmol), 2-(3-methoxy-phenyl)-ethylamine (0.5 mL), EDCI (0.6 g), HOBt (0.4 g) were added to methylene chloride (9 mL), and the reaction mixture was stirred at room temperature for 18 hours. The reaction mixture was partitioned between 1N aqueous HCl and EtOAc, and the combined organic layers were washed with water, dried over Na$_2$SO$_4$, filtered and concentrated under reduced pressure. The residue was purified by flash chromatography (3-20%, 5% NH$_4$OH in MeOH/methylene chloride) to give 1.5 g of 2'-methoxy-5-tetrazol-1-yl-biphenyl-3-carboxylic acid[2-(3-methoxy-phenyl)-ethyl]-amide as a white solid, MS (M+H)=430.

Similarly prepared, but replacing 2-(3-methoxy-phenyl)-ethylamine with 2-(4-methoxy-phenyl)-ethylamine, was 2'-methoxy-5-tetrazol-1-yl-biphenyl-3-carboxylic acid[2-(4-methoxy-phenyl)-ethyl]-amide, MS (M+H)=430.

Similarly prepared, but replacing 2-(3-methoxy-phenyl)-ethylamine with phenyl)-ethylamine, was 2'-methoxy-5-tetrazol-1-yl-biphenyl-3-carboxylic acid phenethyl-amide, MS (M+H)=400.

Similarly prepared, but replacing 2-(3-methoxy-phenyl)-ethylamine with 2-(4-chloro-phenyl)-ethylamine, was 2'-methoxy-5-tetrazol-1-yl-biphenyl-3-carboxylic acid[2-(4-chloro-phenyl)-ethyl]-amide, MS (M+H)=434.

Similarly prepared, but replacing 2-(3-methoxy-phenyl)-ethylamine with 2-(3,4-dichloro-phenyl)-ethylamine was 2'-methoxy-5-tetrazol-1-yl-biphenyl-3-carboxylic acid[2-(3,4-dichloro-phenyl)-ethyl]-amide, MS (M+H)=468.

Similarly prepared, but replacing 2-(3-methoxy-phenyl)-ethylamine with 2-(3-bromo-4-methoxy-phenyl)-ethylamine, was 2'-methoxy-5-tetrazol-1-yl-biphenyl-3-carboxylic acid[2-(3-bromo-4-methoxy-phenyl)-ethyl]-amide, MS (M+H)=509

Similarly prepared, but replacing 2-(3-methoxy-phenyl)-ethylamine with 2-(2-fluoro-phenyl)-ethylamine, was 2'-Methoxy-5-tetrazol-1-yl-biphenyl-3-carboxylic acid[2-(2-fluoro-phenyl)-ethyl]-amide, MS (M+H)=418.

Similarly prepared, but replacing 2-(3-methoxy-phenyl)-ethylamine with 2-(3,4-difluoro-phenyl)-ethylamine, was 2'-methoxy-5-tetrazol-1-yl-biphenyl-3-carboxylic acid[2-(3,4-difluoro-phenyl)-ethyl]-amide, MS (M+H)=436.

Similarly prepared, but replacing 2-(3-methoxy-phenyl)-ethylamine with 2-p-tolyl-ethylamine was 2'-methoxy-5-tetrazol-1-yl-biphenyl-3-carboxylic acid(2-p-tolyl-ethyl)-amide, MS (M+H)=414.

Similarly prepared, but replacing 2-(3-methoxy-phenyl)-ethylamine with 2-o-tolyl-ethylamine was 2'-methoxy-5-tetrazol-1-yl-biphenyl-3-carboxylic acid(2-o-tolyl-ethyl)-amide, MS (M+H)=414.

Similarly prepared, but replacing 2-(3-methoxy-phenyl)-ethylamine with 2-m-tolyl-ethylamine was 2'-methoxy-5-tetrazol-1-yl-biphenyl-3-carboxylic acid(2-m-tolyl-ethyl)-amide, MS (M+H)=414.

Similarly prepared, but replacing 2-(3-methoxy-phenyl)-ethylamine with 2-benzo[1,3]dioxol-5-yl-ethylamine, was 2'-methoxy-5-tetrazol-1-yl-biphenyl-3-carboxylic acid (2-benzo[1,3]dioxol-5-yl-ethyl)-amide, MS (M+H)=444.

Similarly prepared, but replacing 2-(3-methoxy-phenyl)-ethylamine with 2-(3-methanesulfonyl-phenyl)-ethylamine, was 2'-methoxy-5-tetrazol-1-yl-biphenyl-3-carboxylic acid [2-(4-methanesulfonyl-phenyl)-ethyl]-amide, MS (M+H)=480.

Similarly prepared, but replacing 2-(3-methoxy-phenyl)-ethylamine with 2-(4-dimethylamino-phenyl)-ethylamine was 2'-methoxy-5-tetrazol-1-yl-biphenyl-3-carboxylic acid [2-(4-dimethylamino-phenyl)-ethyl]-amide, MP=192.8-194.1° C.

Similarly prepared, but replacing 2-(3-methoxy-phenyl)-ethylamine with 3-(3,3-dimethoxy-phenyl)-propylamine, was 2'-methoxy-5-tetrazol-1-yl-biphenyl-3-carboxylic acid [3-(3,4-dimethoxy-phenyl)-propyl]-amide, MS (M+H)=474.

Similarly prepared, but replacing 2-(3-methoxy-phenyl)-ethylamine with 3,4-dimethoxy-benzylamine, was 2'-methoxy-5-tetrazol-1-yl-biphenyl-3-carboxylic acid 3,4-dimethoxy-benzylamide, MS (M+H)=446.

Similarly prepared, but replacing 2-(3-methoxy-phenyl)-ethylamine with 2-pyridin-2-yl-ethylamine, was 2'-methoxy-5-tetrazol-1-yl-biphenyl-3-carboxylic acid(2-pyridin-2-yl-ethyl)-amide, MS (M+H)=401.

Similarly prepared, but replacing 2-(3-methoxy-phenyl)-ethylamine with 2-pyridin-3-yl-ethylamine, was 2'-methoxy-5-tetrazol-1-yl-biphenyl-3-carboxylic acid(2-pyridin-3-yl-ethyl)-amide, MS (M+H)=401.

Similarly prepared, but replacing 2-(3-methoxy-phenyl)-ethylamine with 2-pyridin-4-yl-ethylamine, was 2'-methoxy-5-tetrazol-1-yl-biphenyl-3-carboxylic acid(2-pyridin-4-yl-ethyl)-amide, MS (M+H)=401.

Additional compounds prepared using the above procedure, but replacing 2'-methoxy-5-tetrazol-1-yl-biphenyl-3-carboxylic acid with other carboxylic acid compounds from Preparation 1, are shown in Table 1.

Example 2

N-[2-(4-Fluoro-phenyl)-ethyl]-3-(3-methoxy-pyridin-2-yl)-5-tetrazol-1-yl-benzamide The synthetic procedure described in this Example was carried out according to the process shown in Scheme F.

SCHEME F

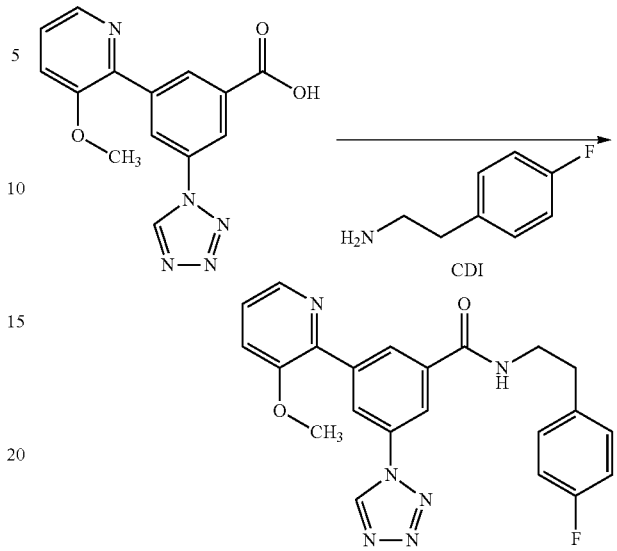

3-(3-Methoxy-pyridin-2-yl)-5-tetrazol-1-yl-benzoic acid (140 mg) and dissolved in dry NMP (15 mL), and CDI (80 mg, 0.49 mmol) was added. The reaction mixture was stirred for 40 minutes, and then 2-(4-fluorophenyl)-ethylamine (0.16 mL, 1.22 mmol) was added. The reaction mixture was stirred for 24 hours at room temperature, and then poured into 30 mL water. The resulting mixture was extracted with EtOAc, and the combined organic layers were washed with water and brine, dried over $Na_2SO_4$, filtered and concentrated under reduced pressure. The residue was purified via flash chromatography using EtOAc/hexanes (30%-100%) to give 15 mg of N-[2-(4-fluoro-phenyl)-ethyl]-3-(3-methoxy-pyridin-2-yl)-5-tetrazol-1-yl-benzamide, MS (M+H)=419.

Similarly prepared, but replacing 2-(4-fluorophenyl)-ethylamine with C-(6-Methoxy-1,2,3,4-tetrahydro-naphthalen-1-yl)-methylamine, was 3-(3-Methoxy-pyridin-2-yl)-N-(7-methoxy-1,2,3,4-tetrahydro-naphthalen-1-ylmethyl)-5-tetrazol-1-yl-benzamide, MP=135.0-136.0° C.

Similarly prepared, but replacing 3-(3-methoxy-pyridin-2-yl)-5-tetrazol-1-yl-benzoic acid with 3-tetrazol-1-yl-5-(5-methanesulfonyl-pyridin-2-yl)-benzoic acid, was N-[2-(2-fluoro-phenyl)-ethyl]-3-(5-methanesulfonyl-pyridin-2-yl)-5-tetrazol-1-yl-benzamide, MS (M+H)=467.

Similarly prepared, but replacing 3-(3-methoxy-pyridin-2-yl)-5-tetrazol-1-yl-benzoic acid with 3-tetrazol-1-yl-5-(2-methoxy-pyrimidin-5-yl)-benzoic acid, was N-[2-(2-fluoro-phenyl)-ethyl]-3-(2-methoxy-pyrimidin-5-yl)-5-tetrazol-1-yl-benzamide, MS (M+H)=420.

Similarly prepared, but replacing 3-(3-methoxy-pyridin-2-yl)-5-tetrazol-1-yl-benzoic acid with 3-tetrazol-1-yl-5-(1-ethyl-pyrrol-3-yl)-benzoic acid, was 3-(1-ethyl-1H-pyrrol-3-yl)-N-[2-(2-fluoro-phenyl)-ethyl]-5-tetrazol-1-yl-benzamide, MS (M+H)=405.

Similarly prepared, but replacing 3-(3-methoxy-pyridin-2-yl)-5-tetrazol-1-yl-benzoic acid with 5-(3-carboxy-5-tetrazol-1-yl-phenyl)-thiophene-2-carboxylic acid tert-butyl ester, was 5-{3-[2-(2-fluoro-phenyl)-ethylcarbamoyl]-5-tetrazol-1-yl-phenyl}-thiophene-2-carboxylic acid tert-butyl ester, MS (M+H)=494.

Example 3

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 4

Nicotinic alpha 7 Modulation Assay

Cell Cultures

Cell Culture Growth Media: F10 medium (Invitrogen), 2.5% Fetal Bovine Serum (FBS, Summit Biotechnology); 15% heat inactivated donor Horse Serum (Invitrogen), 250 µg/ml Hygromycin B (Invitrogen); and 100 nM Methyllicaconite (MLA, Sigma) are added to each new culture by 50-fold dilution of stock solution prepared in $H_2O$ at 5 µM.

$GH_4C_1$ cells (rat pituitary-derived cell line) stably expressing human nicotinic alpha7 WT receptor (RPA clone #34.7) are cultivated in cell culture growth media (described above) at 37 C in a humidified atmosphere containing 4% $CO_2$. Fresh cell stock cultures are initiated with cells at $0.1$-$0.2 \times 10^6$/ml, 50 ml media per T225 flask and are grown for 2 or 3 days prior to use in FLIPR assay. Cells harvested two days after intiation of stock flask typically yields ~25×10⁶/T225 flask and 3 days after intiation of stock flask typically yields ~40×10⁶/T225 flask.

One day prior to assay, cells are placed in in fresh cell culture growth media supplemented with 100 nM fresh MLA. To accomplish media change, suspension cells of the culture are removed and 45 ml fresh cell culture growth media (containing 100 nM fresh MLA) is immediately added to the stock flask as large numbers of cells remain adherent to the surface. The cells in suspension are then collected by centrifugation, resuspended in 5 ml fresh cell culture growth media and returned to the original culture flask.

Buffer Solutions

Buffer solutions used in the assay are HBSS FLIPR buffer (Invitrogen), 2 mM $CaCl_2$ (Sigma), 10 mM HEPES (Invitrogen), 2.5 mM Probenecid (Sigma), and 0.1% BSA (Sigma)

FLIPR Assay

The alpha 7 nAChR assay is a cell-based functional readout designed to determine the effect of test compounds to either directly activate nicotinic receptor channels and/or to modulate activation by the native agonist acetylcholine (ACh, Sigma).

On day one of the assay, attached cells are lifted using 1×-concentration Versene (Gibco, Cat-No. 15040), combined with cells in suspension, and collected by centrifugation (5 min, 162×g). The cell pellet is resuspended in FLIPR buffer at $0.5 \times 10^6$ /ml and cells dispensed into sample wells of a 96-well poly-d-lysine coated black/clear plate (Becton Dickinson) at $0.5 \times 10^5$ cells per well. Sample wells are then supplemented with FLUO-3AM dye (TefLabs, stock solution prepared at 2.5 mM in anhydrous DMSO containing 10% Pluronic acid) in FLIPR buffer at 1 µM final assay concentration (FAC). Dye loading of cells occurs by incubation of plates for one hour at 37 C in a humidified atmosphere containing 4% $CO_2$. To remove extracellular dye, FLIPR plates are washed using a Biotek EL405 plate washer leaving a residual volume of 0.1 ml FLIPR buffer per sample well.

Assay of test compound effect on activation of the alpha7 nicotinic receptor channel is done by measurement of cytosolic [$Ca^{2+}$] elevation as reported by increased FLUO-3 fluorescence using a two addition experimental design and FLIPR™ (Molecular Devices). Following a 30 second baseline recording, test compounds are added online (dilution scheme below) and cell response is recorded for an additional 5 minutes. After a second addition of ACh (30 µM, FAC), plates are read for an additional 4 minutes.

Test Compound Preparation

Multiple concentrations of test compounds are examined in parallel on each 96 well assay plate. In order to achieve 100 µM (1.00E-4 M) for the highest FAC of test compound, 24 µl of 10 mM test compound stock solution (100% DMSO) is added directly to 576 µl of FLIPR buffer (i.e. highest [test compound]=0.4 mM=4-fold FAC). Starting with the 0.4 mM test compound sample, test compounds are then diluted serially in FLIPR buffer (using Biomek 2000) resulting in the following test compound FACs: vehicle, 1.00E-4 M, 3.16E-5, 1.00E-5 M, 3.16E-6, 1.00E-6 M, 3.16E-7, 1.00E-7 M. Maximum FAC for DMSO=1% in the sample wells exposed to the the highest FAC of test compound of 100 µM. Negative controls were madeby vehicle addition, followed by ACh addition. Positive controls were made by 1 µM PNU-120596 addition, followed by ACh addition.

Compound Activity

Values for $IC_{50}/EC_{50}$, intrinsic agonist activity and positive allosteric modulation for alpha 7 nAChR were determined using ACTIVITYBASE™ data analysis software. For dose-response data, either the fitted mid-point of the curve (inflection) or the point at which the curve crosses a threshold activity value (typically 50% of control) may be used to determin $IC_{50}/EC_{50}$.

Using the above assay, the compounds of the invention were determined to be positive allosteric modulators for alpha 7 nAChR. For example, the compound 2'-methoxy-5-tetrazol-1-yl-biphenyl-3-carboxylic acid[2-(4-sulfamoyl-phenyl)-ethyl]-amide showed an $EC_{50}$ of 0.0421, and positive allosteric modulation of 467.65.

Example 5

In Vivo Assay for Asthma and Lung Function

BALb/cJ mice are immunized with a standard immunization protocol. Briefly, mice (N=8/group) are immunized i.p. with ovalbumin (OVA; 10 µg) in alum on days 0 and 14. Mice are then challenged with aerosolized OVA (5%) on day 21 and 22. Animals receive vehicle (p.o.) or a compound of the invention (100 mg/kg p.o.) all starting on day 20.

Lung function is evaluated on day 23 using the Buxco system to measure PenH in response to an aerosol methacholine challenge. Mice are then euthanized and plasma samples collected at the end of the study.

Example 6

Formalin Pain Assay

Male Sprague Dawley rats (180-220 g) are placed in individual Plexiglas cylinders and allowed to acclimate to the testing environment for 30 min. Vehicle, drug or positive control (morphine 2 mg/kg) is administered subcutaneously at 5 ml/kg. 15 min post dosing, formalin (5% in 50 µl) is injected into plantar surface of the right hind paw using a 26-gauge needle. Rats are immediately put back to the observation chamber. Mirrors placed around the chamber allow unhindered observation of the formalin-injected paw. The duration of nociphensive behavior of each animal is recorded by a blinded observer using an automated behavioral timer. Hindpaw licking and shaking/lifting are recorded separately in 5 min bin, for a total of 60 min. The sum of time spent licking or shaking in seconds from time 0 to 5 min is considered the early phase, whereas the late phase is taken as the sum of seconds spent licking or shaking from 15 to 40 min. A plasma sample is collected.

Example 7

Colon Pain Assay

Adult male Sprague-Dawley rats (350-425 g; Harlan, Indianapolis, Ind.) are housed 1-2 per cage in an animal care facility. Rats are deeply anesthetized with pentobarbital sodium (45 mg/kg) administered intraperitoneally. Electrodes are placed and secured into the external oblique musculature for electromyographic (EMG) recording. Electrode leads are tunneled subcutaneously and exteriorized at the nape of the neck for future access. After surgery, rats are housed separately and allowed to recuperate for 4-5 days prior to testing.

The descending colon and rectum are distended by pressure-controlled inflation of a 7-8 cm-long flexible latex balloon tied around a flexible tube. The balloon is lubricated, inserted into the colon via the anus, and anchored by taping the balloon catheter to the base of the tail. Colorectal distension (CRD) is achieved by opening a solenoid gate to a constant pressure air reservoir. Intracolonic pressure is controlled and continuously monitored by a pressure control device. Response is quantified as the visceromotor response (VMR), a contraction of the abdominal and hindlimb musculature. EMG activity produced by contraction of the external oblique musculature is quantified using Spike2 software (Cambridge Electronic Design). Each distension trial lasts 60 sec, and EMG activity is quantified for 20 sec before distension (baseline), during 20 sec distension, and 20 sec after distention. The increase in total number of recorded counts during distension above baseline is defined as the response. Stable baseline responses to CRD (10, 20, 40 and 80 mmHg, 20 seconds, 4 minutes apart) are obtained in conscious, unsedated rats before any treatment.

Compounds are evaluated for effects on responses to colon distension initially in a model of acute visceral nociception and a model of colon hypersensitivity produced by intracolonic treatment with zymosan (1 mL, 25 mg/mL) instilled into the colon with a gavage needle inserted to a depth of about 6 cm. Experimental groups will consist of 8 rats each.

Acute visceral nociception: For testing effects of drug on acute visceral nociception, 1 of 3 doses of drug, vehicle or positive control (morphine, 2.5 mg/kg) are administered after baseline responses are established; responses to distension are followed over the next 60-90 minutes.

Visceral hypersensitivity: For testing effects of drug or vehicle after intracolonic treatment with zymosan, intracolonic treatment is given after baseline responses are established. Prior to drug testing at 4 hours, responses to distension are assessed to establish the presence of hypersensitivity. In zymosan-treated rats, administration of 1 of 3 doses of drug, vehicle or positive control (morphine, 2.5 mg/kg) are given 4 hours after zymosan treatment and responses to distension followed over the next 60-90 minutes.

Example 8

Cold Allodynia in Rats with a Chronic Constriction Injury of the Sciatic Nerve

The effects of compounds of this invention on cold allodynia are determined using the chronic constriction injury (CCI) model of neuropathic pain in rats, where cold allodynia is measured in a cold-water bath with a metal-plate floor and water at a depth of 1.5-2.0 cm and a temperature of 3-4° C. (Gogas, K. R. et al., Analgesia, 1997, 3, 1-8).

Specifically, CCI, rats are anesthetized; the trifurcation of the sciatic nerve is located and 4 ligatures (4-0, or 5-0 chromic gut) are placed circumferentially around the sciatic nerve proximal to the trifurcation. The rats are then allowed to recover from the surgery. On days 4-7 after surgery, the rats are initially assessed for cold-induced allodynia by individually placing the animals in the cold-water bath and recording the total lifts of the injured paw during a 1-min period of time: The injured paw is lifted out of the water. Paw lifts associated with locomotion or body repositioning are not recorded. Rats that displayed 5 lifts per min or more on day 4-7 following surgery are considered to exhibit cold allodynia and are used in subsequent studies. In the acute studies, vehicle, reference compound or compounds of this invention are administered subcutaneously (s.c.) 30 min before testing. The effects of repeated administration of the compounds of this invention on cold allodynia are determined 14, 20 or 38 h following the last oral dose of the following regimen: oral (p.o.) administration of vehicle, reference or a compound of this invention at ~12 h intervals (BID) for 7 days.

Example 9

Cognition Enhancement

The cognition-enhancing properties of compounds of the invention may be in a model of animal cognition: the novel object recognition task model. 4-Month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47-59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula I:

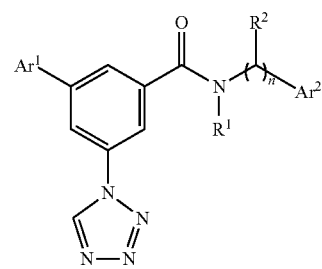

or a pharmaceutically acceptable salt thereof,
wherein:
n is 2;
Ar¹ and Ar² each independently is optionally substituted aryl or optionally substituted heteroaryl;
R¹ is hydrogen or $C_{1-6}$alkyl;
R² is hydrogen, or R² may form an alkylene bridge with Ar²; and
provided that when, R² is hydrogen and Ar¹ is phenyl or 2-methoxy-phenyl, then Ar² is not 4-methoxy-phenyl or 3,4-dimethoxy-phenyl.

2. The compound of claim 1, wherein R¹ is hydrogen.
3. The compound of claim 1, wherein R² is hydrogen.
4. The compound of claim 1, wherein Ar¹ is optionally substituted phenyl.
5. The compound of claim 1, wherein Ar¹ is phenyl optionally substituted one, two or three times, preferably once or twice, with a group or groups independently selected from halo, $C_{1-6}$alkyl, $C_{1-6}$alkoxy, halo-$C_{1-6}$alkyl, $C_{1-6}$alkyl-carbonyl, $C_{1-6}$alkoxy-carbonyl, $C_{1-6}$alkyl-sulfonyl, $C_{1-6}$alkyl-sulfanyl, amino, hydroxy-$C_{1-6}$alkyl, hydroxy, alkylenedioxy and cyano.

6. The compound of claim 1, wherein $Ar^1$ is phenyl optionally substituted once or twice with a group or groups independently selected from fluoro, chloro, methyl, ethyl, methoxy, ethoxy, acetyl, methanesulfonyl, methanesulfanyl, hydroxymethyl, hydroxy, ethoxycarbonyl and cyano.

7. The compound of claim 1, wherein $Ar^1$ is phenyl, 2-methoxy-phenyl, 3-methoxy-phenyl, 4-methoxy-phenyl, 2-chloro-phenyl, 3-chloro-phenyl, 4-chloro-phenyl, 2-methyl-phenyl, 3-methyl-phenyl, 4-methyl-phenyl, 2-fluoro-phenyl, 3-fluoro-phenyl, 4-fluoro-phenyl, 2-ethoxy-phenyl, 2-acetyl-phenyl, 2,3-dimethoxy-phenyl, 2,4-dimethoxy-phenyl, 2,5-dimethoxy-phenyl, 3,4-dimethoxy-phenyl, 3,5-dimethoxy-phenyl, 3,6-dimethoxy-phenyl, 2,3-dichloro-phenyl, 2,4-dichloro-phenyl, 2,5-dichloro-phenyl, 3,4-dichloro-phenyl, 3,5-dichloro-phenyl, 3,6-dichloro-phenyl, 2,3-difluoro-phenyl, 2,4-difluoro-phenyl, 2,5-difluoro-phenyl, 3,4-difluoro-phenyl, 3,5-difluoro-phenyl, 3,6-difluoro-phenyl, 2,3-dimethyl-phenyl, 2,4-dimethyl-phenyl, 2,5-dimethyl-phenyl, 3,4-dimethyl-phenyl, 3,5-dimethyl-phenyl, 3,6-dimethyl-phenyl, 3-chloro-2-methoxy-phenyl, 4-chloro-2-methoxy-phenyl, 5-chloro-2-methoxy-phenyl, 6-chloro-2-methoxy-phenyl, 2-chloro-3-methoxy-phenyl, 4-chloro-3-methoxy-phenyl, 5-chloro-3-methoxy-phenyl, 6-chloro-3-methoxy-phenyl, 2-chloro-4-methoxy-phenyl, 2-chloro-5-methoxy-phenyl, 3-fluoro-2-methoxy-phenyl, 4-fluoro-2-methoxy-phenyl, 5-fluoro-2-methoxy-phenyl, 6-fluoro-2-methoxy-phenyl, 2-fluoro-3-methoxy-phenyl, 4-fluoro-3-methoxy-phenyl, 5-fluoro-3-methoxy-phenyl, 6-fluoro-3-methoxy-phenyl, 2-fluoro-4-methoxy-phenyl, 2-fluoro-5-methoxy-phenyl, 3-methyl-2-methoxy-phenyl, 4-methyl-2-methoxy-phenyl, 5-methyl-2-methoxy-phenyl, 6-methyl-2-methoxy-phenyl, 2-methyl-3-methoxy-phenyl, 4-methyl-3-methoxy-phenyl, 5-methyl-3-methoxy-phenyl, 6-methyl-3-methoxy-phenyl, 2-methyl-4-methoxy-phenyl, 2-methyl-5-methoxy-phenyl, 2-methanesulfanyl-phenyl, 2-methanesulfonyl-phenyl, 2-hydroxy-phenyl, 4-ethoxycarbonyl-phenyl, 2-ethyl-phenyl, 2-cyano-phenyl, or 4-methanesulfonyl-phenyl.

8. The compound of claim 1, wherein $Ar^1$ is 3-methoxyphenyl, 4-methoxy-phenyl, 2-chloro-phenyl, 3-chloro-phenyl, 4-chloro-phenyl, 2-methyl-phenyl, 3-methyl-phenyl, 4-methyl-phenyl, 2-fluoro-phenyl, 3-fluoro-phenyl, 4-fluoro-phenyl, 2-ethoxy-phenyl, 2-acetyl-phenyl, 2,3-dimethoxy-phenyl, 2,4-dimethoxy-phenyl, 2,5-dimethoxy-phenyl, 3,4-dimethoxy-phenyl, 3,5-dimethoxy-phenyl, 3,6-dimethoxy-phenyl, 2,3-dichloro-phenyl, 2,4-dichloro-phenyl, 2,5-dichloro-phenyl, 3,4-dichloro-phenyl, 3,5-dichloro-phenyl, 3,6-dichloro-phenyl, 2,3-difluoro-phenyl, 2,4-difluoro-phenyl, 2,5-difluoro-phenyl, 3,4-difluoro-phenyl, 3,5-difluoro-phenyl, 3,6-difluoro-phenyl, 2,3-dimethyl-phenyl, 2,4-dimethyl-phenyl, 2,5-dimethyl-phenyl, 3,4-dimethyl-phenyl, 3,5-dimethyl-phenyl, 3,6-dimethyl-phenyl, 3-chloro-2-methoxy-phenyl, 4-chloro-2-methoxy-phenyl, 5-chloro-2-methoxy-phenyl, 6-chloro-2-methoxy-phenyl, 2-chloro-3-methoxy-phenyl, 4-chloro-3-methoxy-phenyl, 5-chloro-3-methoxy-phenyl, 6-chloro-3-methoxy-phenyl, 2-chloro-4-methoxy-phenyl, 2-chloro-5-methoxy-phenyl, 3-fluoro-2-methoxy-phenyl, 4-fluoro-2-methoxy-phenyl, 5-fluoro-2-methoxy-phenyl, 6-fluoro-2-methoxy-phenyl, 2-fluoro-3-methoxy-phenyl, 4-fluoro-3-methoxy-phenyl, 5-fluoro-3-methoxy-phenyl, 6-fluoro-3-methoxy-phenyl, 2-fluoro-4-methoxy-phenyl, 2-fluoro-5-methoxy-phenyl, 3-methyl-2-methoxy-phenyl, 4-methyl-2-methoxy-phenyl, 5-methyl-2-methoxy-phenyl, 6-methyl-2-methoxy-phenyl, 2-methyl-3-methoxy-phenyl, 4-methyl-3-methoxy-phenyl, 5-methyl-3-methoxy-phenyl, 6-methyl-3-methoxy-phenyl, 2-methyl-4-methoxy-phenyl, 2-methyl-5-methoxy-phenyl, 2-methanesulfanyl-phenyl, 2-methanesulfonyl-phenyl, 2-hydroxy-phenyl, 4-ethoxycarbonyl-phenyl, 2-ethyl-phenyl, 2-cyano-phenyl, or 4-methanesulfonyl-phenyl.

9. The compound of claim 1, wherein $Ar^1$ is phenyl, 2-methoxy-phenyl, 4-methoxy-phenyl, 4-chloro-phenyl, 4-methyl-phenyl, 2-methyl-phenyl, 2-chloro-phenyl, 2-fluoro-phenyl, 2-ethoxy-phenyl, 2-acetyl-phenyl, 2,4-dimethoxy-phenyl, 3,6-dimethoxy-phenyl, 5-fluoro-2-methoxy-phenyl, 5-chloro-2-methoxy-phenyl, 2,5-dichloro-phenyl, 2-hydroxymethyl-phenyl, 2,3-dichloro-phenyl, 2-methanesulfanyl-phenyl, 2,3-difluoro-phenyl, 2,4-dichloro-phenyl, 2-hydroxy-phenyl, 4-ethoxycarbonyl-phenyl, 2-ethyl-phenyl, 2-cyano-phenyl, 2,3-dimethoxy-phenyl, 4-methoxy-2-methyl-phenyl or 4-methanesulfonyl-phenyl.

10. The compound of claim 1, wherein $Ar^1$ is 4-methoxyphenyl, 4-chloro-phenyl, 4-methyl-phenyl, 2-methyl-phenyl, 2-chloro-phenyl, 2-fluoro-phenyl, 2-ethoxy-phenyl, 2-acetyl-phenyl, 2,4-dimethoxy-phenyl, 3,6-dimethoxy-phenyl, 5-fluoro-2-methoxy-phenyl, 5-chloro-2-methoxy-phenyl, 2,5-dichloro-phenyl, 2-hydroxymethyl-phenyl, 2,3-dichloro-phenyl, 2-methanesulfanyl-phenyl, 2,3-difluoro-phenyl, 2,4-dichloro-phenyl, 2-hydroxy-phenyl, 4-ethoxycarbonyl-phenyl, 2-ethyl-phenyl, 2-cyano-phenyl, 2,3-dimethoxy-phenyl, 4-methoxy-2-methyl-phenyl or 4-methanesulfonyl-phenyl.

11. The compound of claim 1, wherein $Ar^1$ is 2-methoxyphenyl that is optionally substituted once at the 3-, 4-, 5- or 6-position with fluoro, chloro, methyl or methoxy.

12. The compound of claim 1, wherein $Ar^1$ is 2-methoxyphenyl.

13. The compound of claim 1, wherein $Ar^1$ is optionally substituted pyridinyl.

14. The compound of claim 1, wherein $Ar^1$ is pyridinyl optionally substituted once or twice with a group or groups independently selected from halo, $C_{1-6}$alkyl, $C_{1-6}$alkoxy, halo-$C_{1-6}$alkyl, $C_{1-6}$alkyl-carbonyl, $C_{1-6}$alkoxy-carbonyl, $C_{1-6}$alkyl-sulfonyl, aminosulfonyl, $C_{1-6}$alkyl-sulfanyl, hydroxy-$C_{1-6}$alkyl, amino, hydroxy, alkylenedioxy and cyano.

15. The compound of claim 1, wherein $Ar^1$ is pyridinyl optionally substituted once or twice with a group or groups independently selected from fluoro, chloro, methyl, ethyl, methoxy, ethoxy, acetyl, methanesulfonyl, methanesulfanyl, hydroxymethyl, ethoxycarbonyl and cyano.

16. The compound of claim 1, wherein $Ar^1$ is pyridin-2-yl or pyridin-3-yl optionally substituted with methoxy or trifluoromethyl.

17. The compound of claim 1, wherein $Ar^1$ is 3-methoxypyridin-2-yl, 5-trifluoromethyl-pyridin-2-yl or 2-methoxypyridin-3-yl.

18. The compound of claim 1, wherein $Ar^2$ is optionally substituted phenyl.

19. The compound of claim 1, wherein $Ar^2$ is phenyl optionally substituted once or twice with a group or groups independently selected from halo, $C_{1-6}$alkyl, $C_{1-6}$alkoxy, halo-$C_{1-6}$alkyl, $C_{1-6}$alkyl-carbonyl, $C_{1-6}$alkoxy-carbonyl, $C_{1-6}$ alkyl-sulfonyl, $C_{1-6}$alkyl-sulfanyl, hydroxy-$C_{1-6}$alkyl, amino, hydroxy, alkylenedioxy and cyano.

20. The compound of claim 1, wherein $Ar^2$ is phenyl optionally substituted once or twice with a group or groups independently selected from fluoro, chloro, bromo, methyl, methoxy, aminosulfonyl, dimethylamino, methanesulfonyl or methylenedioxy.

21. The compound of claim 1, wherein $Ar^2$ is phenyl, 2-methoxy-phenyl, 3-methoxy-phenyl, 4-methoxy-phenyl, 2-chloro-phenyl, 3-chloro-phenyl, 4-chloro-phenyl, 2-methyl-phenyl, 3-methyl-phenyl, 4-methyl-phenyl, 2-fluoro-phenyl, 3-fluoro-phenyl, 4-fluoro-phenyl, 2-ethoxy-phenyl, 2-acetyl-phenyl, 2,3-dimethoxy-phenyl, 2,4-dimethoxy-phenyl, 2,5-dimethoxy-phenyl, 3,4-dimethoxy-phenyl, 3,5-dimethoxy-phenyl, 3,6-dimethoxy-phenyl, 2,3-dichloro-phenyl, 2,4-dichloro-phenyl, 2,5-dichloro-phenyl, 3,4-dichloro-phenyl, 3,5-dichloro-phenyl, 3,6-dichloro-phenyl, 2,3-difluoro-phenyl, 2,4-difluoro-phenyl, 2,5-difluoro-phenyl, 3,4-difluoro-phenyl, 3,5-difluoro-phenyl, 3,6-difluoro-phenyl, 2,3-dimethyl-phenyl, 2,4-dimethyl-phenyl, 2,5-dimethyl-phenyl, 3,4-dimethyl-phenyl, 3,5-dimethyl-phenyl, 3,6-dimethyl-phenyl, 3-chloro-2-methoxy-phenyl, 4-chloro-2-methoxy-phenyl, 5-chloro-2-methoxy-phenyl, 6-chloro-2-methoxy-phenyl, 2-chloro-3-methoxy-phenyl, 4-chloro-3-methoxy-phenyl, 5-chloro-3-methoxy-phenyl, 6-chloro-3-methoxy-phenyl, 2-chloro-4-methoxy-phenyl, 2-chloro-5-methoxy-phenyl, 3-fluoro-2-methoxy-phenyl, 4-fluoro-2-methoxy-phenyl, 5-fluoro-2-methoxy-phenyl, 6-fluoro-2-methoxy-phenyl, 2-fluoro-3-methoxy-phenyl, 4-fluoro-3-methoxy-phenyl, 5-fluoro-3-methoxy-phenyl, 6-fluoro-3-methoxy-phenyl, 2-fluoro-4-methoxy-phenyl, 2-fluoro-5-methoxy-phenyl, 3-methyl-2-methoxy-phenyl, 4-methyl-2-methoxy-phenyl, 5methyl-2-methoxy-phenyl, 6-methyl-2-methoxy-phenyl, 2-methyl-3-methoxy-phenyl, 4-methyl-3-methoxy-phenyl, 5-methyl-3-methoxy-phenyl, 6-methyl-3-methoxy-phenyl, 2-methyl-4-methoxy-phenyl, 2-methyl-5-methoxy-phenyl, 2-methanesulfanyl-phenyl, 2-hydroxy-phenyl, 4-ethoxycarbonyl-phenyl, 2-ethyl-phenyl, 2-cyano-phenyl, 4-methanesulfonyl-phenyl, 4-aminosulfonyl-phenyl, 4-dimethylamino-phenyl or 3-bromo-4-methoxy-phenyl.

22. The compound of claim 1, wherein $Ar^2$ is phenyl, 2-methoxy-phenyl, 3-methoxy-phenyl, 4-methoxy-phenyl, 2-chloro-phenyl, 3-chloro-phenyl, 4-chloro-phenyl, 2-methyl-phenyl, 3-methyl-phenyl, 4-methyl-phenyl, 2-fluoro-phenyl, 3-fluoro-phenyl, 4-fluoro-phenyl, 2-ethoxy-phenyl, 2-acetyl-phenyl, 2,3-dimethoxy-phenyl, 2,4-dimethoxy-phenyl, 2,5-dimethoxy-phenyl, 3,5-dimethoxy-phenyl, 3,6-dimethoxy-phenyl, 2,3-dichloro-phenyl, 2,4-dichloro-phenyl, 2,5-dichloro-phenyl, 3,4-dichloro-phenyl, 3,5-dichloro-phenyl, 3,6-dichloro-phenyl, 2,3-difluoro-phenyl, 2,4-difluoro-phenyl, 2,5-difluoro-phenyl, 3,4-difluoro-phenyl, 3,5-difluoro-phenyl, 3,6-difluoro-phenyl, 2,3-dimethyl-phenyl, 2,4-dimethyl-phenyl, 2,5-dimethyl-phenyl, 3,4-dimethyl-phenyl, 3,5-dimethyl-phenyl, 3,6-dimethyl-phenyl, 3-chloro-2-methoxy-phenyl, 4-chloro-2-methoxy-phenyl, 5-chloro-2-methoxy-phenyl, 6-chloro-2-methoxy-phenyl, 2-chloro-3-methoxy-phenyl, 4-chloro-3-methoxy-phenyl, 5-chloro-3-methoxy-phenyl, 6-chloro-3-methoxy-phenyl, 2-chloro-4-methoxy-phenyl, 2-chloro-5-methoxy-phenyl, 3-fluoro-2-methoxy-phenyl, 4-fluoro-2-methoxy-phenyl, 5-fluoro-2-methoxy-phenyl, 6-fluoro-2-methoxy-phenyl, 2-fluoro-3-methoxy-phenyl, 4-fluoro-3-methoxy-phenyl, 5-fluoro-3-methoxy-phenyl, 6-fluoro-3-methoxy-phenyl, 2-fluoro-4-methoxy-phenyl, 2-fluoro-5-methoxy-phenyl, 3-methyl-2-methoxy-phenyl, 4-methyl-2-methoxy-phenyl, 5-methyl-2-methoxy-phenyl, 6-methyl-2-methoxy-phenyl, 2-methyl-3-methoxy-phenyl, 4-methyl-3-methoxy-phenyl, 5-methyl-3-methoxy-phenyl, 6-methyl-3-methoxy-phenyl, 2-methyl-4-methoxy-phenyl, 2-methyl-5-methoxy-phenyl, 2-methanesulfanyl-phenyl, 2-hydroxy-phenyl, 4-ethoxycarbonyl-phenyl, 2-ethyl-phenyl, 2-cyano-phenyl, 4-methanesulfonyl-phenyl, 4-aminosulfonyl-phenyl, 4-dimethylamino-phenyl or 3-bromo-4-methoxy-phenyl.

23. The compound of claim 1, wherein $Ar^2$ is phenyl, 3-methoxy-phenyl, 4-methoxy-phenyl, 3,4-dimethoxy-phenyl, 4-aminosulfonyl-phenyl, 4-chloro-phenyl, 3,4-dichloro-phenyl, 3-bromo-4-methoxy-phenyl, 2-fluoro-phenyl, 3,4-difluoro-phenyl, 4-methyl-phenyl, 3-methyl-phenyl, 4-fluoro-phenyl, 4-dimethylamino-phenyl, 2-methyl-phenyl, 3,4-ethylenedioxy-phenyl or 4-methanesulfonylphenyl.

24. The compound of claim 1, wherein $Ar^2$ is phenyl, 3-methoxy-phenyl, 4-methoxy-phenyl, 4-aminosulfonyl-phenyl, 4-chloro-phenyl, 3,4-dichloro-phenyl, 3-bromo-4-methoxy-phenyl, 2-fluoro-phenyl, 3,4-difluoro-phenyl, 4-methyl-phenyl, 3-methyl-phenyl, 4-fluoro-phenyl, 4-dimethylamino-phenyl, 2-methyl-phenyl, 3,4-ethylenedioxy-phenyl or 4-methanesulfonylphenyl.

25. The compound of claim 1, wherein $Ar^2$ is optionally substituted pyridinyl.

26. The compound of claim 1, wherein $Ar^2$ is pyridinyl optionally substituted once or twice with a group or groups independently selected from halo, $C_{1-6}$alkyl, $C_{1-6}$alkoxy, halo-$C_{1-6}$alkyl, $C_{1-6}$alkyl-carbonyl, $C_{1-6}$alkoxy-carbonyl, $C_{1-6}$alkyl-sulfonyl, $C_{1-6}$alkyl-sulfanyl, hydroxy-$C_{1-6}$alkyl, amino, hydroxy, alkylenedioxy and cyano.

27. The compound of claim 1, wherein $Ar^2$ is pyridinyl optionally substituted once or twice with a group or groups independently selected from fluoro, chloro, bromo, methyl, methoxy, aminosulfonyl, methanesulfonyl or methylenedioxy.

28. The compound of claim 1, wherein $Ar^2$ is pyridin-2-yl, pyridin-3-yl or pyridin-4-yl.

29. A compound selected from the group consisting of:
2'-Methoxy-5-tetrazol-1-yl-biphenyl-3-carboxylic acid phenethyl-amide;
2'-Methoxy-5-tetrazol-1-yl-biphenyl-3-carboxylic acid [2-(4-methoxy-phenyl)-ethyl]-amide;
2'-Methoxy-5-tetrazol-1-yl-biphenyl-3-carboxylic acid [2-(3-methoxy-phenyl)-ethyl]-amide;
2'-Methoxy-5-tetrazol-1-yl-biphenyl-3-carboxylic acid [2-(4-sulfamoyl-phenyl)-ethyl]-amide;
2'-Methoxy-5-tetrazol-1-yl-biphenyl-3-carboxylic acid [2-(4-chloro-phenyl)-ethyl]-amide;
2'-Methoxy-5-tetrazol-1-yl-biphenyl-3-carboxylic acid [2-(3,4-dichloro-phenyl)-ethyl]-amide;
2'-Methoxy-5-tetrazol-1-yl-biphenyl-3-carboxylic acid [2-(3-bromo-4-methoxy-phenyl)-ethyl]-amide;
2'-Methoxy-5-tetrazol-1-yl-biphenyl-3-carboxylic acid [2-(2-fluoro-phenyl)-ethyl]-amide;
2'-Methoxy-5-tetrazol-1-yl-biphenyl-3-carboxylic acid [2-(3,4-difluoro-phenyl)-ethyl]-amide;
2'-Methoxy-5-tetrazol-1-yl-biphenyl-3-carboxylic acid (2-p-tolyl-ethyl)-amide;
2'-Methoxy-5-tetrazol-1-yl-biphenyl-3-carboxylic acid (2-o-tolyl-ethyl)-amide;
2'-Methoxy-5-tetrazol-1-yl-biphenyl-3-carboxylic acid (2-benzo[1,3]dioxo5-yl-ethyl)-amide;
2'-Methoxy-5-tetrazol-1-yl-biphenyl-3-carboxylic acid (2-m-tolyl-ethyl)-amide;
4'-Methoxy-5-tetrazol-1-yl-biphenyl-3-carboxylic acid [2-(3,4-dimethoxy-phenyl)-ethyl]-amide;
4'-Chloro-5-tetrazol-1-yl-biphenyl-3-carboxylic acid [2-(3,4-dimethoxy-phenyl)-ethyl]-amide;
4'-Methyl-5-tetrazol-1-yl-biphenyl-3-carboxylic acid [2-(3,4-dimethoxy-phenyl)-ethyl]-amide;
2'-Methyl-5-tetrazol-1-yl-biphenyl-3-carboxylic acid [2-(3,4-dimethoxy-phenyl)-ethyl]-amide;
2'-Chloro-5-tetrazol-1-yl-biphenyl-3-carboxylic acid [2-(3,4-dimethoxy-phenyl)-ethyl]-amide;

2'-Fluoro-5-tetrazol-1-yl-biphenyl-3-carboxylic acid [2-(3,4-dimethoxy-phenyl)-ethyl]-amide;
2'-Ethoxy-5-tetrazol-1-yl-biphenyl-3-carboxylic acid [2-(3,4-dimethoxy-phenyl)-ethyl]-amide;
2'-Acetyl-5-tetrazol-1-yl-biphenyl-3-carboxylic acid [2-(3,4-dimethoxy-phenyl)-ethyl]-amide;
2',4'-Dimethoxy-5-tetrazol-1-yl-biphenyl-3-carboxylic acid [2-(3,4-dimethoxy-phenyl)-ethyl]-amide;
2',5'-Dimethoxy-5-tetrazol-1-yl-biphenyl-3-carboxylic acid [2-(3,4-dimethoxy-phenyl)-ethyl]-amide;
5'-Fluoro-2'-methoxy-5-tetrazol-1-yl-biphenyl-3-carboxylic acid [2-(3,4-dimethoxy-phenyl)-ethyl]-amide;
5'-Chloro-2'-methoxy-5-tetrazol-1-yl-biphenyl-3-carboxylic acid [2-(3,4-dimethoxy-phenyl)-ethyl]-amide;
2',5'-Dichloro-5-tetrazol-1-yl-biphenyl-3-carboxylic acid [2-(3,4-dimethoxy-phenyl)-ethyl]-amide;
2'-Hydroxymethyl-5-tetrazol-1-yl-biphenyl-3-carboxylic acid [2-(3,4-dimethoxy-phenyl)-ethyl]-amide;
2',3'-Dichloro-5-tetrazol-1-yl-biphenyl-3-carboxylic acid [2-(3,4-dimethoxy-phenyl)-ethyl]-amide;
2'-Methylsulfanyl-5-tetrazol-1-yl-biphenyl-3-carboxylic acid [2-(3,4-dimethoxy-phenyl)-ethyl]-amide;
2',3'-Difluoro-5-tetrazol-1-yl-biphenyl-3-carboxylic acid [2-(3,4-dimethoxy-phenyl)-ethyl]-amide;
2',4'-Dichloro-5-tetrazol-1-yl-biphenyl-3-carboxylic acid [2-(3,4-dimethoxy-phenyl)-ethyl]-amide;
2'-Hydroxy-5-tetrazol-1-yl-biphenyl-3-carboxylic acid [2-(3,4-dimethoxy-phenyl)-ethyl]-amide;
5'-[2-(3,4-Dimethoxy-phenyl)-ethylcarbamoyl]-2-nitro-3'-tetrazol-1-yl-biphenyl-4-carboxylic acid ethyl ester;
2'-Ethyl-5-tetrazol-1-yl-biphenyl-3-carboxylic acid [2-(3,4-dimethoxy-phenyl)-ethyl]-amide;
2'-Cyano-5-tetrazol-1-yl-biphenyl-3-carboxylic acid [2-(3,4-dimethoxy-phenyl)-ethyl]-amide;
2',3'-Dimethoxy-5-tetrazol-1-yl-biphenyl-3-carboxylic acid [2-(3,4-dimethoxy-phenyl)-ethyl]-amide;
4'-Methoxy-2'-methyl-5-tetrazol-1-yl-biphenyl-3-carboxylic acid [2-(3,4-dimethoxy-phenyl)-ethyl]-amide;
2'-Methoxy-5-tetrazol-1-yl-biphenyl-3-carboxylic acid [2-(4-dimethylamino-phenyl)-ethyl]-amide;
2'-Methoxy-5-tetrazol-1-yl-biphenyl-3-carboxylic acid [2-(4-methanesulfonyl-phenyl)-ethyl]-amide;
4'-Methylsulfanyl-5-tetrazol-1-yl-biphenyl-3-carboxylic acid [2-(2-fluoro-phenyl)-ethyl]-amide;
2'-Methoxy-5-tetrazol-1-yl-biphenyl-3-carboxylic acid [3-(3,4-dimethoxy-phenyl)-propyl]-amide;
2'-Methoxy-5-tetrazol-1-yl-biphenyl-3-carboxylic acid 3,4-dimethoxy-benzylamide;
2'-Methoxy-5-tetrazol-1-yl-biphenyl-3-carboxylic acid (2-pyridin-3-yl-ethyl)-amide;
2'-Methoxy-5-tetrazol-1-yl-biphenyl-3-carboxylic acid (2-pyridin-4-yl-ethyl)-amide;
2'-Methoxy-5-tetrazol-1-yl-biphenyl-3-carboxylic acid (2-pyridin-2-yl-ethyl)-amide;
N-[2-(2-Fluoro-phenyl)-ethyl]-3-(3-methoxy-pyridin-2-yl)-5-tetrazol-1-yl-benzamide;
N-[2-(2-Fluoro-phenyl)-ethyl]-3-tetrazol-1-yl-5-(5-trifluoromethyl-pyridin-2-yl)-benzamide;
N-[2-(3,4-Dimethoxy-phenyl)-ethyl]-3-(2-methoxy-pyridin-3-yl)-5-tetrazol-1-yl-benzamide;
2'-Methoxy-5-tetrazol-1-yl-biphenyl-3-carboxylic acid (7-methoxy-1,2,3,4-tetrahydro-naphthalen-1-ylmethyl)-amide;
3-(3-Methoxy-pyridin-2-yl)-N-(7-methoxy-1,2,3,4-tetrahydro-naphthalen-1-ylmethyl)-5-tetrazol-1-yl-benzamide;
N-[2-(2-Fluoro-phenyl)-ethyl]-3-(5-methanesulfonyl-pyridin-2-yl)-5-tetrazol-1-yl-benzamide;
N-[2-(2-Fluoro-phenyl)-ethyl]-3-(2-methoxy-pyrimidin-5-yl)-5-tetrazol-1-yl-benzamide;
3-(1-Ethyl-1H-pyrrol-3-yl)-N-[2-(2-fluoro-phenyl)-ethyl]-5-tetrazol-1-yl-benzamide; and
5-{3-[2-(2-Fluoro-phenyl)-ethylcarbamoyl]-5-tetrazol-1-yl-phenyl}-thiophene-2-carboxylic acid tert-butyl ester.

\* \* \* \* \*